United States Patent [19]

Rutherford et al.

[11] Patent Number: 4,521,541

[45] Date of Patent: Jun. 4, 1985

[54] PROCESS FOR FORMING FUNCTIONAL FLUID AND SOLID-CONTAINING THERMOPLASTIC FILMS, USES THEREOF AND PROCESS FOR PRODUCING SAME

[75] Inventors: Howard J. Rutherford, Kinnelon; Donald A. Withycombe, Lincroft, both of N.J.

[73] Assignee: International Flavors & Fragrances Inc., New York, N.Y.

[21] Appl. No.: 465,313

[22] Filed: Feb. 9, 1983

[51] Int. Cl.$^3$ .............................................. B29D 27/00
[52] U.S. Cl. ........................................ 521/79; 106/243; 252/174.11; 252/174.13; 264/50; 264/DIG. 5; 425/4 C; 521/82; 521/97; 521/99; 521/113; 521/114
[58] Field of Search ............... 264/53, 50, 267, 271.1, 264/279.1, 259, 51, DIG. 5; 106/243; 524/563, 296; 252/134, 174.11, 174.13, 174, 367; 521/79, 82, 97, 99, 113, 116; 425/4 C

[56] References Cited

U.S. PATENT DOCUMENTS

| | | | |
|---|---|---|---|
| 1,441,315 | 1/1923 | Walbridge | 252/134 X |
| 1,583,303 | 5/1926 | Mentz | 261/53 |
| 1,707,334 | 4/1929 | Unfried | 252/174 |
| 2,387,730 | 10/1945 | Alderson, Jr. | 521/143 |
| 2,860,377 | 11/1958 | Whitfield, Jr. et al. | 264/50 |
| 2,948,664 | 8/1960 | Rubens et al. | 204/159.18 |
| 2,948,665 | 8/1960 | Rubens et al. | 204/159.18 |
| 2,967,128 | 1/1961 | Kare | 167/16 |
| 3,067,147 | 12/1962 | Rubens et al. | 521/79 |
| 3,268,636 | 8/1966 | Angell, Jr. | 264/51 |
| 3,287,477 | 11/1966 | Vesilind | 264/53 |
| 3,298,975 | 1/1967 | Feild et al. | 521/143 |
| 3,413,230 | 11/1968 | Dupuis | 252/174 X |
| 3,474,176 | 10/1969 | Freeman | 424/331 |
| 3,505,432 | 4/1970 | Neuwalel | 523/102 |
| 3,725,311 | 4/1973 | Grubb | 524/296 X |
| 3,755,208 | 8/1973 | Ehrenfreund | 264/53 |
| 3,755,360 | 8/1973 | Houlihan | 260/245.7 |
| 3,758,425 | 9/1973 | Jastrow | 425/4 |
| 3,759,641 | 9/1973 | Irmmel | 425/4 R |
| 3,768,234 | 10/1973 | Hardison | 55/223 |
| 3,787,542 | 1/1974 | Gallagher et al. | 264/53 X |
| 3,926,655 | 12/1975 | Miles | 106/270 X |
| 3,975,350 | 8/1976 | Hudgin et al. | 524/108 |
| 4,023,942 | 5/1977 | Brady et al. | 55/241 |
| 4,043,772 | 8/1977 | Lundy | 55/220 |
| 4,051,159 | 9/1977 | Tsoucalas et al. | 524/602 X |
| 4,095,031 | 6/1978 | Engle | 524/563 X |
| 4,137,279 | 1/1979 | Smith et al. | 525/411 |
| 4,143,105 | 3/1979 | Hentschel et al. | 264/51 |
| 4,156,067 | 5/1979 | Gould | 528/73 |
| 4,165,293 | 8/1979 | Gordon | 252/118 |
| 4,181,632 | 1/1980 | Schebece | 252/542 |
| 4,184,099 | 1/1980 | Lindauer et al. | 106/243 X |
| 4,217,319 | 8/1980 | Komori | 264/DIG. 5 |
| 4,247,498 | 1/1981 | Castro | 264/41 |
| 4,255,550 | 3/1981 | Gould | 528/65 |
| 4,256,726 | 3/1981 | Kato et al. | 424/2 X |
| 4,277,358 | 7/1981 | Hopkins | 252/174 X |
| 4,328,319 | 5/1982 | Osipow et al. | 264/53 X |
| 4,369,227 | 1/1983 | Hahn et al. | 428/407 |
| 4,369,267 | 1/1983 | Keung et al. | 523/351 |
| 4,369,291 | 1/1983 | Arlt et al. | 525/247 |
| 4,388,272 | 6/1983 | Gesteland | 424/2 X |
| 4,411,855 | 10/1983 | Fiebig, Jr. et al. | 264/267 X |

FOREIGN PATENT DOCUMENTS

| | | | |
|---|---|---|---|
| 907998 | 8/1972 | Canada | 252/174 |
| 1101165 | 5/1981 | Canada . | |
| 1137069 | 12/1982 | Canada . | |
| 1137068 | 12/1982 | Canada . | |
| 1137067 | 12/1982 | Canada . | |
| 1137066 | 12/1982 | Canada . | |
| 1137065 | 12/1982 | Canada . | |
| 1139737 | 1/1983 | Canada . | |
| 1139738 | 1/1983 | Canada . | |
| 2007413 | 8/1970 | Fed. Rep. of Germany | 252/174 |
| 1520790 | 5/1973 | Fed. Rep. of Germany . | |
| 1629296 | 12/1973 | Fed. Rep. of Germany . | |
| 2401284 | 7/1975 | Fed. Rep. of Germany | 252/174 |
| 1044397 | 9/1966 | United Kingdom . | |
| 1307387 | 2/1973 | United Kingdom | 252/174 |
| 1589201 | 5/1981 | United Kingdom . | |

OTHER PUBLICATIONS

Fred Schrafft, "Extruding Thermoplastic Foams", Modern Plastics Encyclopedia, 1982–1983 Edt. Publ. by McGraw-Hill Publ. Co., 274–275, pp. 246–267 & 332–349.

Calvin J. Benning, "Plastic Foams: The Physics and Chemistry of Product Performance and Process Technology/vol. II: Structure, Properties, and Applications", Publ. by Wiley–Interscience, N.Y., 1969, pp. 261, 264–344, 21–25, 80–93.
1981 Annual Report of International Flavors & Fragrances.
Chem. Abstracts, 1982, vol. 97, 145570y.
Chem. Abstracts, 1982, vol. 96, 123625x, 143750n, and 182506g.

*Primary Examiner*—Philip Anderson
*Attorney, Agent, or Firm*—Arthur L. Liberman

[57] ABSTRACT

Described is a process for preparing extruded functional fluid and solid-containing thermoplastic foamed particles using chemical blowing agents or direct gas extrusion processes, uses of such foamed particles and articles produced from said foamed particles. The process described involves the use of a single screw or double screw extruder wherein the resin particles are added upstream from the functional fluid or solid which, in turn, is added to the extruder upstream from the point of addition of the liquid or gaseous blowing agent.

9 Claims, 37 Drawing Figures

FIG.IA
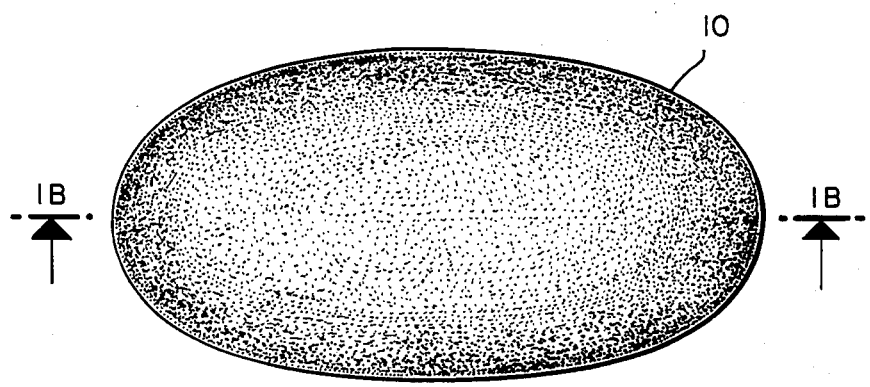
FIG.IB
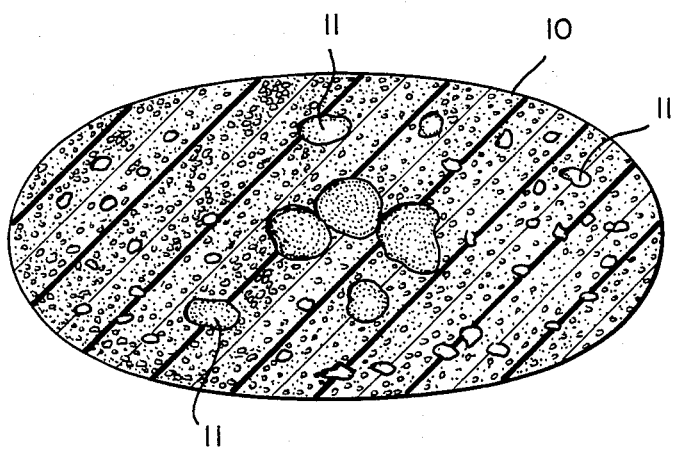

FIG.4
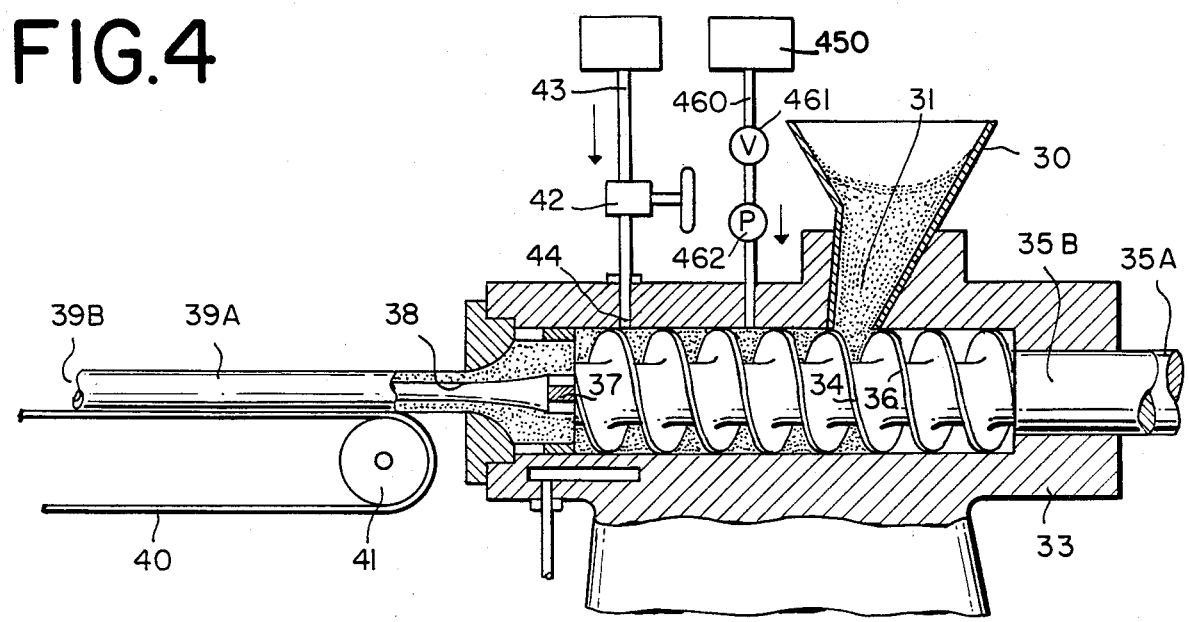
FIG.5A
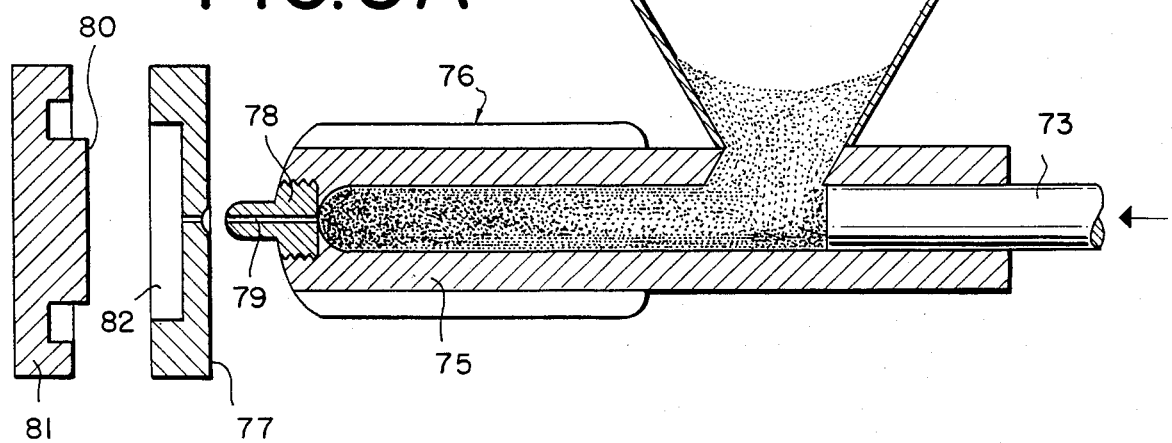
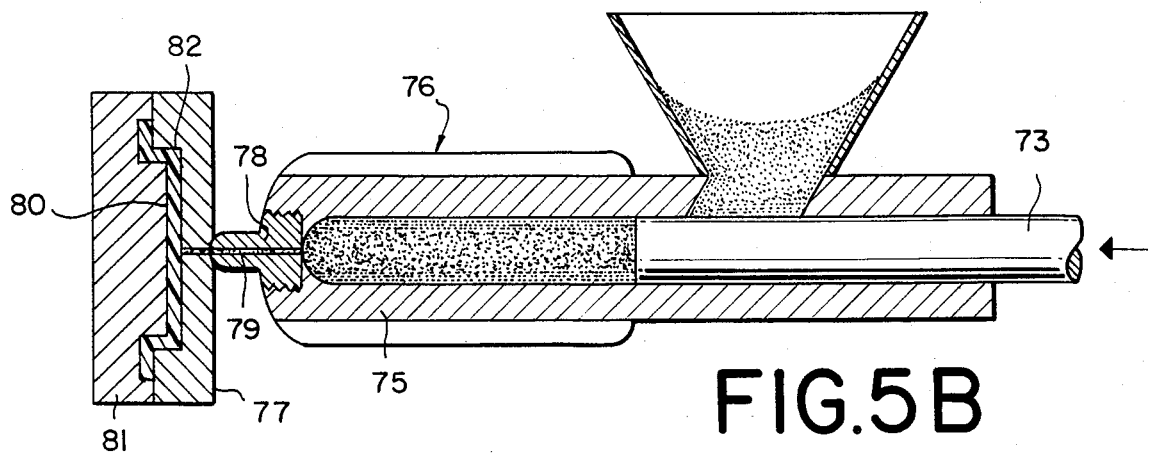
FIG.5B

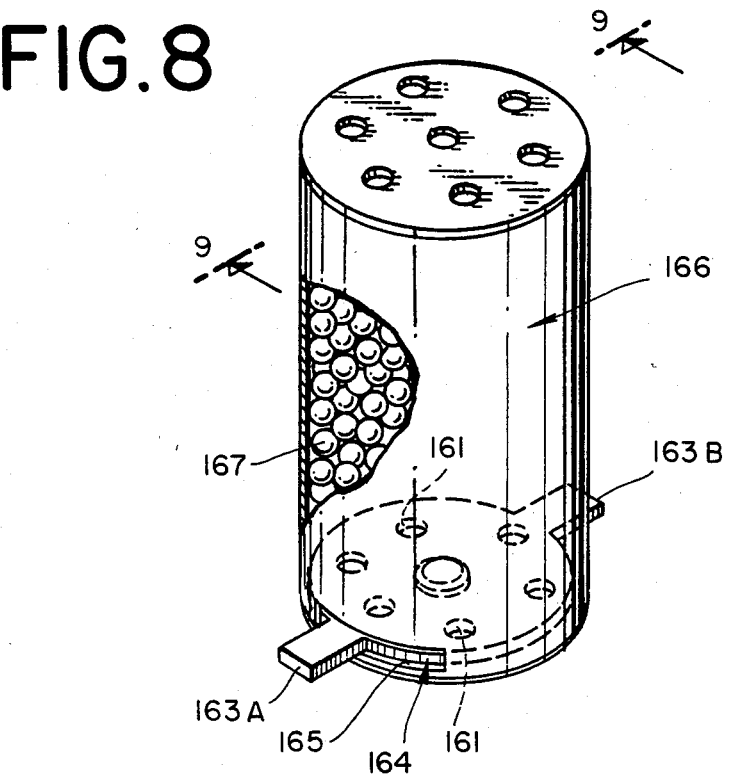
FIG. 8
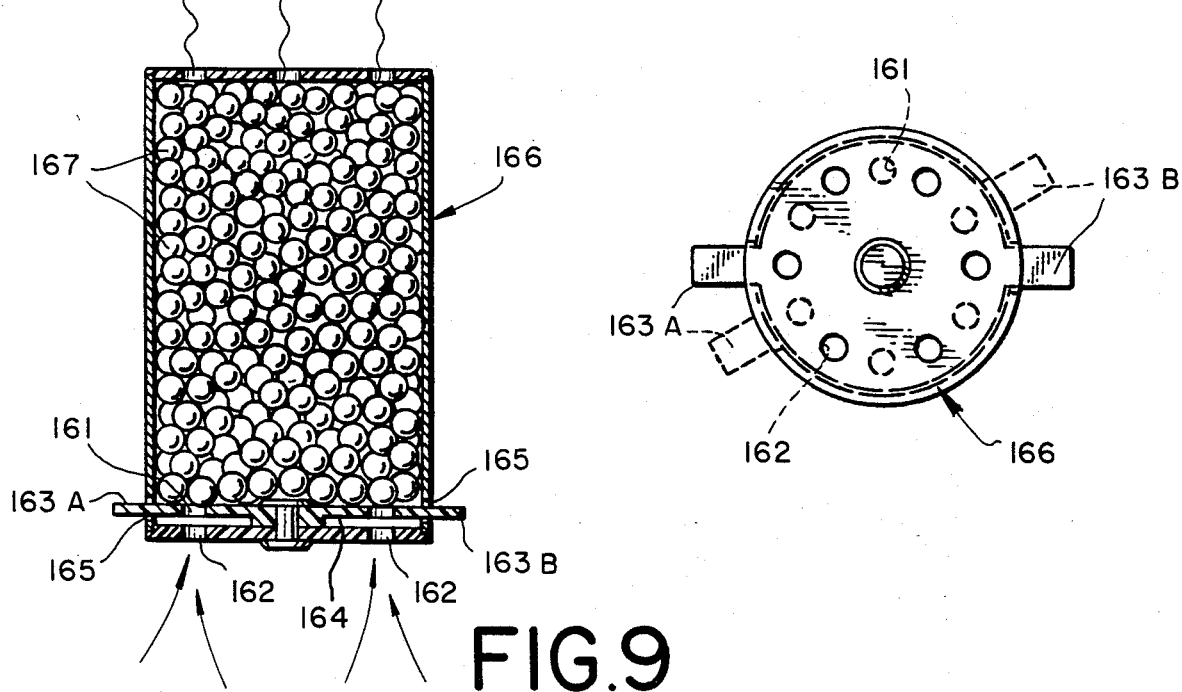
FIG. 9
FIG. 10

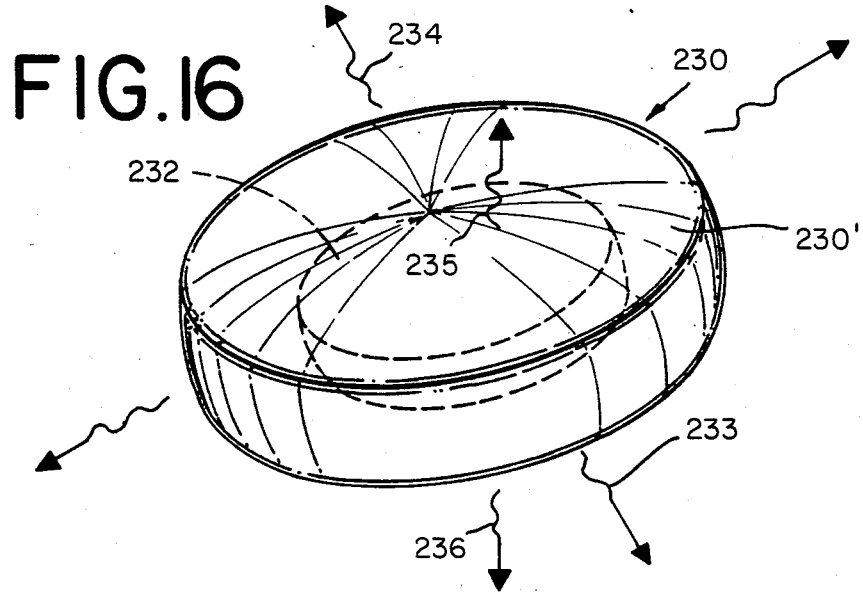
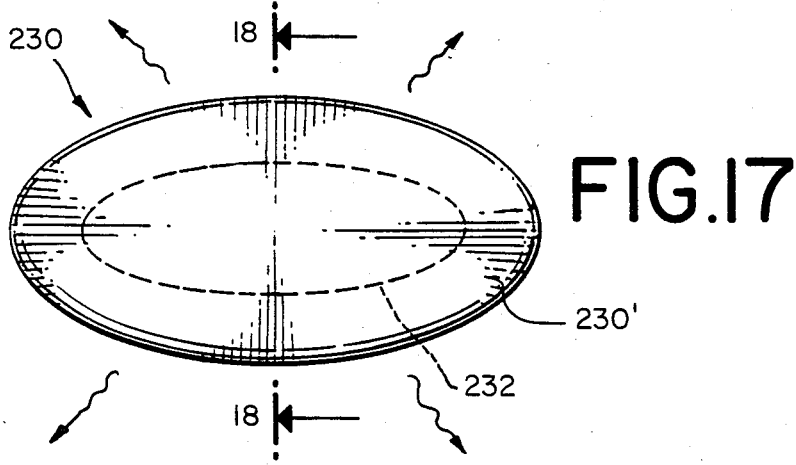
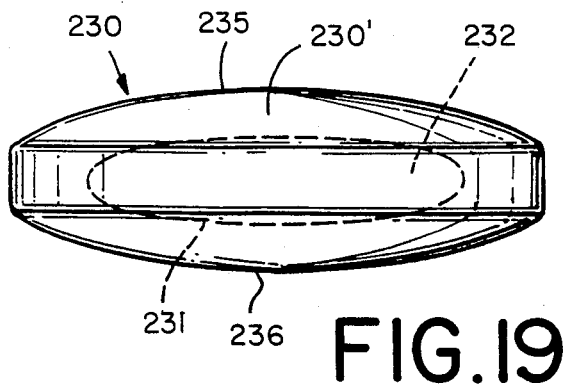
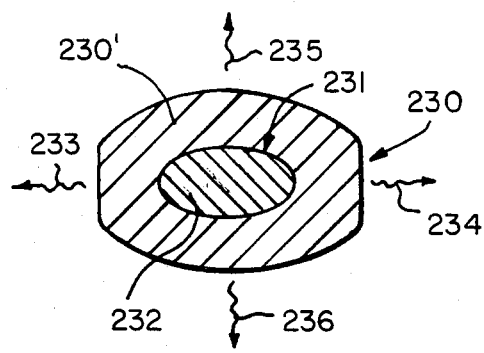

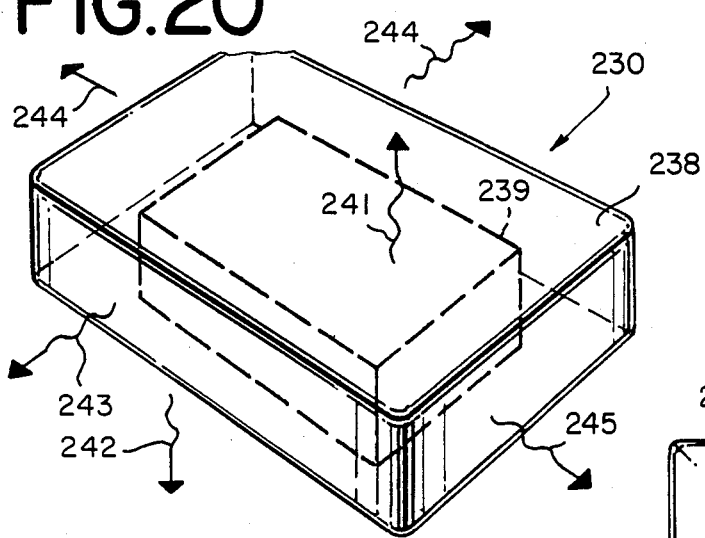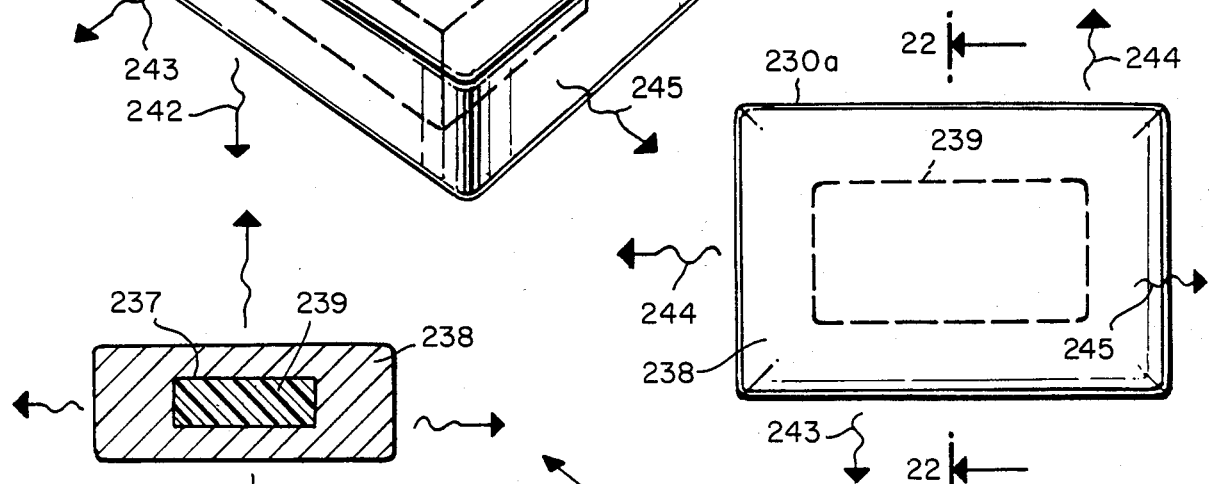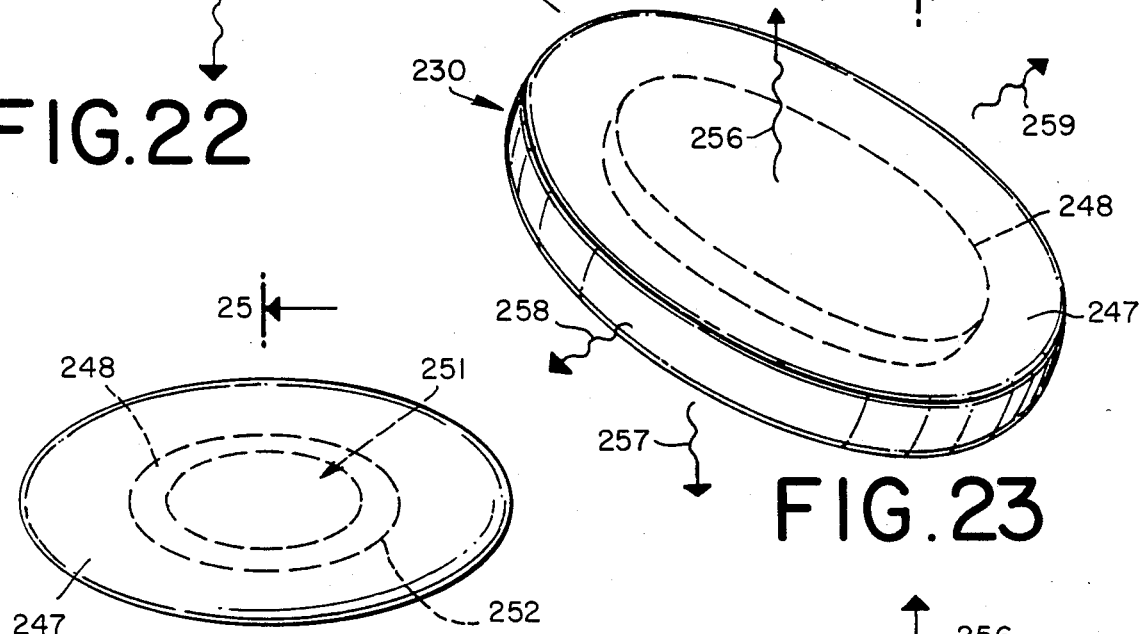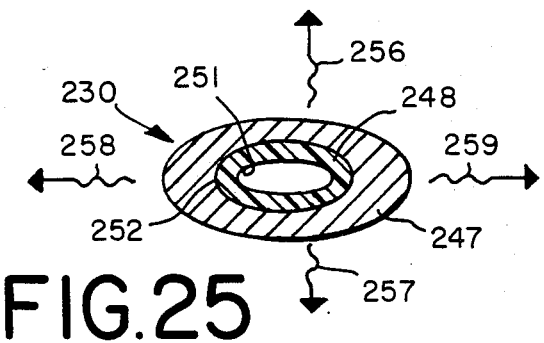

PROCESS FOR FORMING FUNCTIONAL FLUID AND SOLID-CONTAINING THERMOPLASTIC FILMS, USES THEREOF AND PROCESS FOR PRODUCING SAME

BACKGROUND OF THE INVENTION

This invention relates to the production of and use of thermoplastic polymeric foamed particles as controlled release compositions for use in controlled release devices for controlled release of diagnostic materials and/or insect repellents and/or animal repellents and/or aroma augmenting or enhancing compositions. The process for producing such foamed particles containing such functional fluids or solids involves the use of a single screw or twin screw extruder and placing the resin, functional fluid or solid and gaseous or liquid blowing agent into the extruder stream at specific ranges of lateral intervals.

An ever increasing requirement in the medical diagnosis field as well as in the perfume, animal repellent and insect repellent industries exists for a slow controlled release device for slowly and controllably releasing diagnostic compositions for diagnosing physiological malfunctions or aberrations in mammalian species, animal repellents, insect repellents and/or perfume materials into a gaseous environment in order to aid in the diagnosis of such malfunctions or aberrations and/or to aesthetically scent the said environment and/or in order to repel insects and/or in order to repel mammalian species, e.g. deer, coyote, dogs and the like.

Slow release polymers containing perfumes are well known in the prior art. Thus, United Kingdom Patent Specification No. 1,589,201 assigned to Hercules, Inc. discloses a thermoplastic resin body consisting of a thermoplastic polymer of ethylene and 6-60 weight percent of a polar vinyl monomer selected from the group consisting of vinyl acetate, methyl acrylate, ethyl acrylate, butyl acrylate and acrylic acid wherein the perfumed resin body is suitable for the preparation of shaped objects from which perfume odor emanates over a prolonged period at a stable level.

U.S. Pat. No. 3,505,432 discloses a method of scenting a polyolefin which comprises:

(a) mixing a first amount of liquid polyolefin, e.g. polyethylene or polypropylene with a relatively large amount of scent-imparting material to form a flowable mass;

(b) forming drops from said mass and causing substantially instantaneous solidification of said drops into polyolefin pellets having a relatively large amount of scent-imparting material imprisoned therein;

(c) melting said pellets with a second amount of said polyolefin, said second amount being larger than said first amount; and (d) solidifying the melt of (c).

U.S. Pat. No. 4,247,498 issued on Jan. 27, 1981 discloses microporous polymers which are capable of containing volatile substances such as perfumes and the like in forms ranging from films to blocks in intricate shapes from synthetic thermoplastic polymers such as olefinic, condensation or oxidation polymers. In one embodiment of U.S. Pat. No. 4,247,498 the microporous polymers are characterized by relatively homogeneous three-dimensional cellular structure having cells connected by pores of smaller dimension. Also disclosed in U.S. Pat. No. 4,247,498 is a process for making microporous polymers from such thermoplastic polymers by heating a mixture of the polymer and a compatible liquid (e.g., a perfume substance or the like) to form a homogeneous solution, cooling said solution under non-equilibrium thermodynamic conditions to initiate liquid-liquid phase separation, and continuing said cooling until the mixture achieves substantial handling strength. Also disclosed in said U.S. Pat. No. 4,247,498 are microporous polymer products which contain relatively large amounts of such functionally useful fluids as perfume compositions and behave as solids.

U.S. Pat. No. 4,156,067 issued on May 22, 1979 discloses polyurethane polymers characterized by a molecular weight of above 6,000 and having lactone groups and hydroxyl groups in the polymer backbone being prepared by reacting a mixture of polyols, a polyfunctional lactone (e.g. epsilon caprolactone) and a polyfunctional isocyanate proportioned so as to provide certain desired polymer properties. It is indicated in said U.S. Pat. No. 4,156,067 that the product is soluble in alkaline solutions and may be used for light sensitive photographic layers on films, paper or glass; in drug delivery systems, as burn dressings, in body implants such as vascular prosthesis, in molding compositions, and in the manufacture of catheters as well as in delivery of perfume compositions in a slow release manner. It is further indicated in said U.S. Pat. No. 4,156,067 that the water absorptivity of the polyurethane/lactone polymers is above 10%, preferably in the range of about 20% to 60%, and these polymers may range in their physical properties from rigid solids to completely gel-like high water absorptive polymers. It is further indicated in said U.S. Pat. No. 4,156,067 that the polymers provide a leachable substrate wherein the leaching agent may be water, gases, alcohols, esters and body fluids, e.g. animal or human.

Extrusion of thermoplastic foams is well known in the prior art. Thus, the Modern Plastics Encyclopedia (published by the McGraw-Hill Publishing Company) 1982-1983 edition at pages 274 and 275 discloses a section authored by Fred Schrafft entitled "Extruding Thermoplastic Foams". Said article on pages 274 and 275 is incorporated herein by reference. It is indicated therein that three different processes are used for the extrusion of thermoplastic foams:

(i) extrusion of expandable beads
(ii) extrusion of thermoplastics containing a chemical blowing agent and
(iii) direct gas extrusion process.

It is further indicated in the Schrafft article that the extrusion using a chemical blowing agent may be carried out on a normal single screw extruder and the direct gas extrusion process may be carried out on single and twin screw extruders. It is further indicated in the Schrafft article that common blowing agents used in the process are hydrocarbons such as pentene or fluorocarbons such as 11, 12 and 114. It is further stated that:

"the amount of blowing agent can vary widely depending on the resin and the type of product desired. However, generally about 7% blowing agent produces a product of about 5.6 lbs/cu. ft. while 18% blowing agent produces a product of about 1.9 lbs/cu. ft. . . . "

U.S. Pat. No. 3,755,208 (the specification for which is incorporated by reference herein) discloses a process for avoidance of cell collapse in an extrusion process for a copolymer based on a low molecular weight alpha olefin and polar vinyl monomer whereby there is incorporated into the polymer a small amount of partial ester of a long chain fatty acid and a polyol. Federal Republic of Germany Pat. No. 1,520,790 discloses expandable polystyrene beads incorporating polyethylene or polypropylene whereby the expandable polystyrene beads are prepared by aqueous suspension polymerization of styrene with the addition of a vaporizable blowing agent, the polymerization being carried out in the presence of from 0.01 up to 1.0 weight percent polyethylene or polypropylene having a molecular weight of less than 4,000. The publication date of this German patent is May 30, 1973.

Foamable styrene polymers are indicated to be prepared according to U.S. Pat. No. 3,758,425, the disclosure of which is incorporated by reference herein. In U.S. Pat. No. 3,758,425 a process is disclosed for preparing foamable styrene polymer beads containing blowing agents with a particularly favorable narrow grain size distribution, the process comprising the use of copolymers of N-vinyl-N-alkyl acetamide having from 1 to 4 carbon atoms in the alkyl group with an ester of acrylic, methacrylic, malaic or fumaric acid with an aliphatic alcohol having a linear or branched chain and containing from 6 to 18 carbon atoms, as protective colloid in the homo- or copolymerization of styrene in an aqueous suspension in the presence of a blowing agent.

U.S. Pat. No. 3,759,641, the disclosure of which is incorporated by reference herein, as well as U.S. Pat. No. 3,577,360, the disclosure of which is incorporated by reference herein, discloses a process and apparatus for pre-expanding polymer particles to a predetermined density which particles are subject to further expansion. Thus, there is disclosed agitated particulate expandable polymer which is heated in a dry atmosphere in a closed vessel, under vacuum, to a predetermined density. To achieve ultra-low density expandable prepuff, a coolant such as water is introduced into the closed vessel after the predetermined density is reached, but prior to the release of the vacuum. Following release of the vacuum, the beads are removed from the closed vessel and may be molded directly without any aging period such as that necessary following steam pre-expansion.

German Pat. No. 1629296 published on Feb. 20, 1973, the disclosure for which is incorporated by reference herein, discloses the production of particles of foam polyethylene by exposure to an inert gas whereby the density is reduced. Thus, particles of closed cell film polyethylene are obtained by extruding an ethylene polymer in the presence of a foaming agent, e.g. isobutane. After extrusion, the product is exposed to an inert gas under high pressure at up to 20° C. below the melting point of the polymer. The inert gas has a permeability coefficient equal to or less than that of air.

U.S. Pat. No. 3,067,147 issued on Dec. 4, 1962 (Rubens, et al) assigned to Dow Chemical Company discloses the use of 1,2-dichlorotetrafluoroethane which can be injected into polyethylene during extrusion to produce an extruded gel which spontaneously expands as it is extruded into a reduced pressure. A special technique, such as cooling, has been used to produce a stable polyethylene foam as disclosed in said U.S. Pat. No. 3,067,147, the specification for which is incorporated by reference herein. The Rubens, et al patent describes an extrusion process for producing low density (0.04 grams/cm$^3$) polyethylene foams. The variables that influence the mechanical properties of these materials are disclosed in Rubens and Skochdopole in J. Cellular Plastics, January 1965 at pages 91–96, the disclosure of which is incorporated herein by reference.

As disclosed at page 269 of the text "Plastic Foams: the physics and chemistry of product performance and process technology", Volume 1: Chemistry and Physics of Foam Formation, author: Calvin J. Benning published by Wiley-Interscience, a division of John Wiley and Sons, N.Y., (copy in U.S. Patent and Trademark Office Scientific Library), a process for continuous extrusion of expansion of medium density (20–30 lbs. per cu. ft.) polyethylene and sheet has been commercialized by the Nippon Art Paper Company of Japan. The process consists of three steps:

1. preparing pellets impregnated with a foaming agent in solution;
2. feeding the coated pellets into the extruder;
3. extruding into the desired shape.

The key to the development of the Nippon Art Paper Company process is the use of polyethylene "expandable" pellets which can be converted into film or sheet on standard polyethylene blown-film equipment. The pellets can also be blow-molded into bottles or tubes. It is further indicated in the Benning textbook that polyethylene foamed sheet has entered such markets as greenhouse insulation, tablecloths, bags, synthetic leather, wallpaper, tents, toys and packaging.

Other "ethafoam" patents whereby expanded extruded foamed polyethylene having a cell size of 0.5–1.0 mm are indicated to be produced are set forth in Rubens, et al. U.S. Pat. Nos. 2,948,664 and Rubens, et al. 2,948,665, the disclosures for which are incorporated by reference herein.

Additional details concerning methods for producing various foams of various dimensions in various polymers are set forth in Benning "Plastic Foams: the physics and chemistry of product performance and process technology/Volume II: Structure Properties, and Applications", author: Calvin J. Benning, Wiley-Interscience a division of John Wiley and Sons, N.Y., copyright 1969 (copy available in United States Patent & Trademark Office scientific library), the disclosure of which is incorporated by reference herein. Of particular importance are the following pages in the Benning texts:

Volume I: pages 261–344 inclusive
Volume II: pages 20–25, 80–85, 90–93.

U.S. Pat. No. 2,860,377 issued on Nov. 18, 1958 (Bernhardt and Whitfield) discloses the production of a foamed polyethylene by dissolving a gas such as nitrogen therein at elevated pressure while the said plastic is being advanced through an extruder barrel by the action of a rotating extrusion screw, and thereafter releasing the plastic through a die whereby a plastic foam is produced.

In U.K. Patent Specification No. 1,044,397 published on Sept. 28, 1966, it is disclosed that as blowing agents for making foamed polyolefins, it is possible to employ all conventional inorganic and organic compounds which evolve a blowing gas, e.g. nitrogen or carbon dioxide, and it is further disclosed that the polyolefins to be foamed according to the invention have blowing agents which are known per se and, optionally, dyestuffs and/or pigments incorporated therein.

Nothing in the prior art, however, discloses the advantages of the simultaneous foamed pellet/functional fluid or solid imparting of the process of our invention.

BRIEF DESCRIPTION OF THE DRAWINGS

FIG. 1A represents a perspective view of the outside of a foamed polymeric particle containing functional fluid or solid produced according to the process of Example I wherein a nitrogen foaming agent and an aromatizing agent were added to an extruder during the extrusion of polyethylene.

FIG. 1B is a cut-away side elevation view of the particle of FIG. 1A.

FIG. 4 is a cut-away side elevation view of extrusion apparatus used for extruding thermoplastic polymeric foamed tubing containing within the walls of the tubing functional fluid or solid.

FIGS. 5A and 5B represent cut-away side elevation views of injection molding apparatus prior to and during the injection molding operation for the injection molding of the functional fluid or solid-containing foamed polymeric pellets produced according to the process of our invention.

FIG. 5A shows the apparatus immediately prior to the carrying out of the injection molding process and FIG. 5B shows the apparatus during the injection molding process wherein the polymeric foamed pellets are being fused and pushed through the injection molding apparatus orifice into the mold.

FIG. 8 is a partially cut-away perspective view of an article of manufacture useful in the operation of the apparatus of FIGS. 7, 8, 9 and 10 containing foamed polymeric particles containing functional fluid or solid produced using the apparatus of FIG. 2, for example, said polymeric particles containing a functional fluid or solid, e.g. diagnostic composition, perfumery ingredient, insect repellent or animal repellent.

FIG. 9 is a cut-away side elevation view of the article of manufacture of FIG. 8 looking in the direction of the arrows.

FIG. 10 is a top view of the article of manufacture of FIG. 8.

FIG. 16 is a perspective view of an ellipsoidally-shaped detergent tablet containing a solid core which includes fused foamed polymeric particles which is aromatized and, if desired, also containing an additional polymer which may or may not be aromatized, e.g. polyethylene.

FIG. 17 is the top view of the ellipsoidally-shaped detergent tablet of FIG. 16.

FIG. 18 is a cut-away front view of the ellipsoidally-shaped detergent tablet of FIG. 16 in the direction of the arrows in FIG. 17.

FIG. 19 is a side view of the ellipsoidally-shaped detergent tablet of FIG. 16.

FIG. 20 is a perspective view of a rectangular parallelepiped-shaped detergent tablet containing a rectangular parallelepiped-shaped core comprising a major proportion of fused foamed polymeric particles which are aromatized and, if desired, an additional polymer which may or may not be aromatized.

FIG. 21 is a top view of the rectangular parallelepiped-shaped detergent tablet of FIG. 20.

FIG. 22 is a cut-away front view of the rectangular parallelepiped-shaped tablet of FIG. 20 looking in the direction of the arrows in FIG. 21.

FIG. 23 is a perspective view of an ellipsoidally-shaped detergent tablet containing a hollow aroma-imparting agent containing core which includes fused foamed polymeric particles containing aromatizing agent of our invention or, in the alternative, a hollow core of fused foamed polymer produced according to the process of our invention wherein the aroma imparting agent is in the solid polymer and not in the void of the plastic core.

FIG. 24 is a top view of the ellipsoidally-shaped detergent tablet of FIG. 23.

FIG. 25 is a front cut-away view of the ellipsoidally-shaped detergent tablet of FIG. 23 looking in the direction of the arrows in FIG. 24, the core thereof being hollow and either containing an aroma-imparting liquid or, in the alternative, being a hollow core wherein the aroma-imparting material is in the solid fused filmed polymeric particles which make up the core and wherein the void does not contain anything.

SUMMARY OF THE INVENTION

Figure 2:
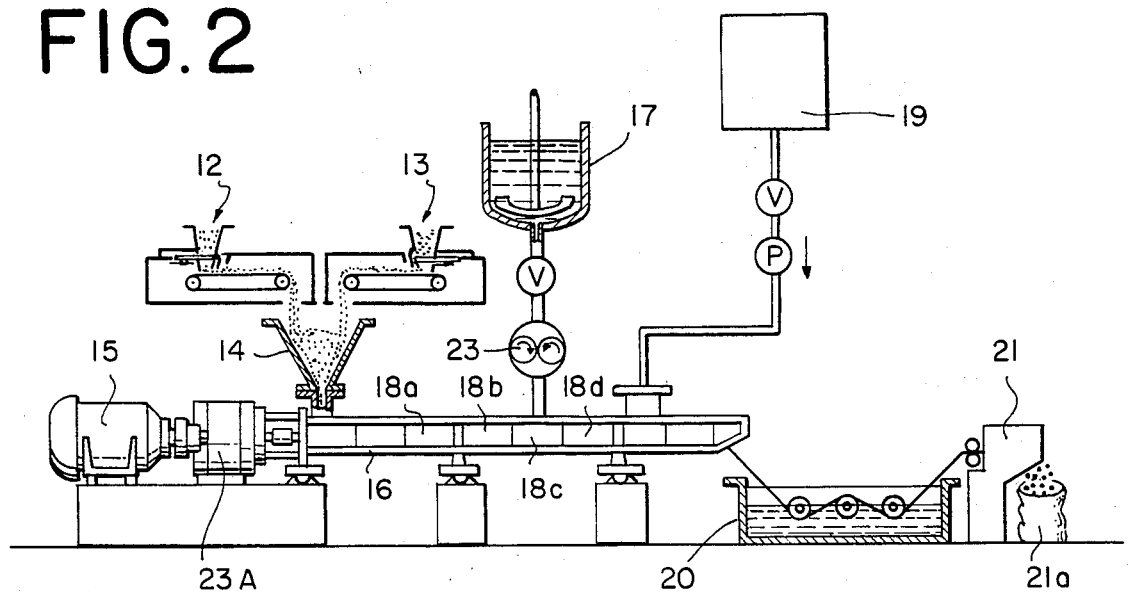
FIG. 2 is a cut-away side elevation schematic diagram of a screw extruder during the compounding of the resin with the functional fluid or solid while simultaneously adding foaming agent into the hollow portion of the barrel of the extruder and incorporates the pelletizing apparatus used in pelletizing the extruded foamed tow produced as a result of the extrusion operation.

Our invention relates to the formation of foamed functional fluid or solid-containing polymeric pellets by means of introduction into a single screw or twin screw extruder of, in series, thermoplastic polymer followed by functional fluid or solid which is compatible with a thermoplastic polymer, in turn, followed by introduction of a gaseous blowing agent or blowing agent which will produce a gas which is inert to the polymer and to the functional fluid or solid previously introduced into the extruder.

The advantages of using the foamed polymeric particles are multiple, to wit: improved handling; greater retention of functional fluid or solid when not in use; greater length of time during which release of functional fluid or solid from polymer is at "steady state" or "zero order".

The nature of the extruder utilized in the process of our invention to form the foamed polymeric functional fluid or solid containing polymer particles of our invention may be either single screw or double screw. Thus, the types of extruders that can be used are disclosed at pages 246–267 and 332–349 of the Modern Plastics Encyclopedia, 1982–1983 published by the McGraw-Hill Publishing Company, the disclosure of which is incorporated by reference herein. More specifically, examples of extruders which are usable in carrying out the process of our invention (with modification for introduction of functional fluid or solid downstream from introduction of the polymer and with a further modification that the gaseous blowing agent is introduced still further downstream from the point of introduction of the functional fluid or solid are as follows:

1. The Welex "Super Twinch" 3.5" extruder manufactured by Welex Incorporated, 850 Jolly Road, Blue Bell, Pa. 19422

2. Krauss-Maffei twin screw extruder manufactured by the Krauss-Maffei Corporation/Extruder Division, 3629 West 30th Street South, Wichita, Kans. 67277

3. Modified Sterling model 4000 and 5000 series extruder manufactured by Sterling Extruder Corporation of 901 Durham Avenue, South Plainfield, N.J.

4. CRT ("Counter-Rotating Tangential") Twin Screw Extruder manufactured by Welding Engineers, Inc. of King of Prussia, Pa. 19406

5. The Leistritz Twin Screw Dispersion Compounder manufactured by the American Leistritz Extruder Corporation of 198 U.S. Route 206 South, Somerville, N.J. 08876

6. The ZSK Twin Screw Co-Rotating Extruder manufactured by the Werner & Pfleiderer Corporation of 663 East Crescent Avenue, Ramsey, N.J. 07446

7. The Farrel Extruder manufactured by Farrel Connecticut Division, Emhart Machinery Group, Ansonia, Conn. 06401

8. The MPC/V Baker Perkins Twin Screw Extruder manufactured by the Baker Perkins Inc. Chemical Machinery Division of Saginaw, Mich. 48601

9. The Berstorff single screw, twin screw, or foam extrusion equipment manufactured by Berstorff Corporation, P.O. Box 240357, 8200-A Arrowridge Blvd., Charlotte, N.C. 28224

In producing the foamed functional fluid or solid-containing polymer particles of our invention, various polymers may be utilized, for example, low density polyethylene, high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolzyed co-polymer of ethylene and vinyl acetate. Preferred co-polymers are ethylene vinyl acetate with about 9 to 60% vinyl acetate and ethylene/ethyl acrylate with about 6 to 18% ethyl acrylate.

Resins of the type disclosed for use as co-polymers are commercially available in the molding powder form. For example, ethylene vinyl acetate co-polymers are marketed by the E. I. duPont de Nemours Company under the tradename "ELVAX ®" and by the Arco Polymer Division under the trademark "DYLAND" and by the Exxon Corporation of Linden, N.J. under the trademark "DEXXON". Ethylene/ethyl acrylate co-polymers are marketed by Union Carbide Corporation under the tradename "EEA RESINS".

The polymer is added to the single screw or twin screw extruder at a feed rate in the range of from about 80 up to about 300 pounds per hour while maintaining the temperature in the screw extruder between about 160° and about 240° C. If the polymer or co-polymer powder is added to the extruder at a reference "barrel segment", then the functional fluid or solid is added to the extruder under pressure downstream from the addition point of the polymer at 1 or more of "barrel segments" 2–9.

Thus, the invention provides a process for forming functional fluid or solid containing foamed polymeric particles such as foamed polymeric pellets which include a relatively high concentration of a material having a particular function, e.g. a selected scent or aroma or a diagnostic material which can be used to diagnose physiological or psycological malfunctions or aberrations in mammalian species, an air freshener, an animal repellent, a bird repellent, an insect repellent, an insect pheremone, an animal pheremone or an environmental deodorizing agent. The functional fluid or solid added at "barrel segments" 2–9 of the single screw or twin screw extruder then has one or more of the foregoing functions. Furthermore, the functional fluid or solid added at barrel segments 2–9 must be previously or made to be compatible with the polymer added at barrel segment 1 of the single screw or twin screw extruder.

More specifically, the perfume oil suitable for our invention includes substantially any of the conventional fragrance materials. These are complex mixtures of volatile compounds including esters, ethers, aldehydes, alcohols, unsaturated alcohols, terpines, saturated and unsaturated ketones, lactones, and cyclic ketones which are well known to those skilled in the fragrance art. Also includable in such mixtures are natural and synthetic "essential oils". An example of a "natural" essential oil is oak moss absolute.

The use as to type and proportion is limited only by either (a) their solubility in the resin or mixture of resins used and/or (b) the volume ratio of microvoids in the polymer to said polymer and/or (c) the solubility of the perfume in the polymer on solidification. The proportion of perfume can in many instances go up to 45% by weight.

Thus, the proportion of perfume oil or other functional fluid or solid to resin, accordingly, can vary from small but effective amounts on the order of about 1% of the weight of the resin body up to about 45% by weight of the resin body. In general, it is preferred to use between about 5% up to about 30% based on the weight of the resin body of functional fluid or solid. This is an optimum amount balancing the proportion of functional fluid or solid, e.g. perfume oil, in the product against the time period over which the article emits the functional fluid or solid, e.g. odor, and against the tendency of the functional fluid or solid, e.g. perfume to "oil out". This "oiling out" is specifically avoided as a result of the use of the foaming agent discussed infra.

Examples of animal repellents useful as functional fluids or solids in conjunction with all aspects of our invention are set forth in U.S. Pat. No. 3,474,176 issued on Oct. 21, 1969, the specification for which is incorporated by reference herein. In this respect, our invention provides safe, effective compositions for controlling mammalian species whereby the materials can be in the form of sheets or strips of polymer containing the animal repellent tied about trees, plants and the like.

Briefly, the animal repellents useful in our invention comprise a suitable carrier compatible with the resins, e.g. polyethylenes or polypropylenes and, if desired, copolymers admixed therewith and an aliphatic or alicyclic ketone, for example, containing from about 6 to 20 carbon atoms. The ketones are present in the composition in amounts effective to repel animals from the area in which the polymeric sheet is placed. The method of our invention comprises placing such a polymeric sheet containing an aliphatic or alicyclic ketone having from about 6 up to about 20 carbon atoms in the area where the mammalian species roams. The effective repellent substances are ketones which contain preferably from about 7 up to about 19 carbon atoms. The ketones can be saturated or unsaturated, aliphatic or alicyclic materials. The ketones desirably used in our invention are examplified by ethylbutyl ketone, methylisoamyl ketone, geranyl acetone, ethyl-n-amyl ketone, methyloctyl ketone, heptylidene acetone, isobutylheptyl ketone, methylundecyl ketone, methylhexyl ketone and 2-methyl-6-heptanone. Preferred ketones are ethylbutyl ketone, methylisoamyl ketone and 4-t-amylcyclohexanone.

In place of, or in addition to, the animal repellents set forth supra, bird repellents can be used in a similar manner with our invention with the polymer composition of our invention in formulating the foamed polymeric particles of our invention. Such bird repellents are set forth in U.S. Pat. No. 2,967,128 issued on Jan. 3, 1961, the specification for which is incorporated by reference herein. As used herein "birds" are members of the class "Aves". Birds both domestic and wild such as chickens, turkeys, ducks, pheasants, crows, etc. cause much damage from an economic standpoint by eating newly planted seeds, ripening grain crops, stored corn, berries, fruits, etc.

Our invention thus utilizes esters of anthranilic acids, esters of phenyl acetic acid and dimethyl benzyl carbinol acetate as bird repellents which are compatible with the polymers which we use in forming the foamed functional fluid or solid-containing polymeric particles of our invention.

Thus, esters useful in conjunction with our invention are esters of phenyl acetic acid and include such wide varieties of ester moieties as alkyl, alkenyl, aryl, aralkyl and the like. The alkyl phenyl acetates specifically exemplified are methyl phenyl acetate, ethyl phenyl acetate and isobutyl phenyl acetate. Insofar as the anthranilates are concerned as bird repellents, the optimum preferred ester for use in conjunction with the polymers used in conjunction with our invention is dimethyl anthranilate (methyl ortho-N-methylaminobenzoate). Other anthranilates or ethyl anthranilates are phenyl ethyl anthranilate, methyl anthranilate and menthyl anthranilate.

As stated supra, various polymers are useful in the practice of our invention. Specific examples of polymers useful in the practice of our invention are as follows:

(a) DYLAN® brand of low density polyethylene (DYLAN® is a trademark owned by the Atlantic Richfield Company of Los Angeles, Calif.

(b) DYLITE® of expandable polystyrene compositions. DYLITE® is a trademark of the Atlantic Richfield Company of Los Angeles, Calif.

(c) SUPER DYLAN® of high density polyethylene. SUPER DYLAN® is a trademark of the Atlantic Richfield Company of Los Angeles, Calif.

(d) Blended polyethylene and carbon black as specifically taught in U.S. Pat. No. 4,369,267 issued on Jan. 18, 1983, the specification for which is incorporated by reference herein.

(e) Polystyrene as disclosed in U.S. Pat. No. 4,369,227 issued on Jan. 18, 1983, the specification for which is incorporated by reference herein.

(f) Polyene/alpha-olefin copolymers as exemplified and disclosed in U.S. Pat. No. 4,369,291, the specification for which is incorporated by reference herein.

(g) Poly-alpha-olefins as exemplified in Canadian Letters Patent No. 1,137,069 issued on Dec. 7, 1982, the specification for which is incorporated by reference herein.

(h) Polymeric compositions as disclosed in Canadian Letters Patent No. 1,137,068 issued on Dec. 7, 1982, the specification for which is incorporated by reference herein.

(i) Poly-alpha-olefins disclosed in Canadian Letters Patent No. 1,137,067, the specification for which is incorporated by reference herein.

(j) Polyolefins described in Canadian Letters Patent No. 1,137,066, the specification for which is incorporated by reference herein.

(k) Polyethylene oxides as disclosed in Canadian Letters Patent No. 1,137,065 issued on Dec. 7, 1982, the specification for which is incorporated by reference herein.

(l) Olefin polymers and co-polymers as disclosed in Canadian Letters Patent No. 1,139,737, the disclosure of which is incorporated by reference herein. Canadian Pat. No. 1,139,737 was issued on Jan. 18, 1983.

(m) Polyolefins disclosed in Canadian Letters Patent No. 1,139,738, the specification for which is incorporated by reference herein. Canadian Pat. No. 1,139,738 was issued on Jan. 18, 1983.

(n) Chlorinated PVC as disclosed in *Polymer* 1982, 23 (7, Suppl.), 1051-6 abstracted at Chem. Abstracts 97:145570y, 1982.

(o) Polyepsilon caprolactone co-polymers made by means of alcohol initiated polymerization as disclosed in *J. Polym. Sci. Polym. Chem. Ed.* 1982, 20(2), pages 319-26, abstracted at Chem. Abstracts, Volume 96:123625x, 1982.

(p) Styrene acrylonitrile co-polymers as disclosed in Diss. Abstracts, Int. B, 1982, 42(8),3346 and abstracted at Chem. Abstracts 96:143750n (1982).

(q) Co-polymers of epsilon caprolactone with 1,4-butane diol as disclosed at Kauch. Rezine, 1982, (2), 8-9, abstracted at Chem. Abstracts, Volume 96:182506g (1982).

(r) Polyesters as disclosed in U.S. Pat. No. 4,326,010, the specification for which is incorporated by reference herein.

(s) Chlorinated polyethylene as disclosed by Belorgey, et al. *J. Polym. Sci.* Polym. Phys. Ed. 1982, 20(2), 191-203.

(t) Plasticized polyepsilon caprolactone co-polymers containing dimethyl phthalate plasticizers as set forth in Japanese Pat. No. J81/147844, abstracted at Chem. Abstracts, Volume 96:69984y (1982), the specification for which is incorporated by reference herein.

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein.

(v) Polyurethane polymers having lactone backbones as disclosed in U.S. Pat. No. 4,156,067 issued on May 22, 1979, the disclosure of which is incorporated by reference herein.

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein.

(x) Resins having polyurethane backbones as disclosed in U.S. Pat. No. 3,975,350 issued on Aug. 17, 1976, the disclosure of which is incorporated by reference herein.

Downstream from the addition point of the functional fluid or solid in the extruder, the gaseous or liquid containing blowing agent may be added (e.g. at barrel segments 5-10, using the polymer addition barrel segment as a reference barrel segment "1". Examples of gaseous blowing agents are carbon dioxide, nitrogen, mixtures of nitrogen and carbon dioxide in proportions from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g. hydrogen, should be avoided. The pressure of the gas blowing agent being added to the extruder at the point of the addition may vary from about 80 up to about 150 psig. Higher pressures may be used without adversely affecting the usefulness of the foamed functional fluid or solid-containing polymer particle.

The feed rate range of functional fluid or solid may be between about 0.5% up to about 45% by weight of the polymer.

The die of the extruder may create rod, sheet, film or ribbon. The resulting product may then, if desired, be pelletized to form foamed functional fluid-containing polymer particles or the ribbon may be used as is as a foamed functional fluid or solid-containing polymeric article of manufacture itself.

In addition to the gaseous blowing agents (which are necessarily "inert" gases), blowing agents may be added at the same point on the extruder which will create gaseous voids in the functional fluid or solid-containing polymeric articles of our invention and these "blowing agents" are well known to one having ordinary skill in the art. Examples of such non-gaseous containing materials which yield gases on admixture with the polymer in the extruder but which are still inert to the functional fluid or solid are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein.

(ii) Ordinarily liquid materials such as n-pentane, isopentane, cyclopentane, hexane and petroleum ether fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, lines 1-5, the specification for which is incorporated by reference herein.

(iii) Dichlorotetrafluoroethane, tetramethylmethane, monochlorodifluoromethane, dichlorodifluoromethane, and dichlorotetrafluoroethane as specifically described in U.S. Pat. Nos. 2,948,664 and 2,948,665 issued on Aug. 9, 1960, the specifications for which are incorporated herein by reference.

(iv) Azo bis(formamide); diazoaminobenzene; N,N'-dinitrosopentamethylene tetramine; N,N'-dimethyl-N,N'-dinitrosoterephthalamide; p,p'-xy-bis(benzene sulfonyl semicarbazide); azo bis(isobutyronitrile); p,p'-oxy-bis(benzene sulfonyl hydrazide); p,p'-diphenyl-bis (sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be for example injection molded to form a useful article. Such injection molding can be carried out in accordance with the procedure as set forth in U.S. Pat. No. 3,268,636 issued on Aug. 23, 1966, the specification for which is incorporated by reference herein.

DETAILED DESCRIPTION OF THE DRAWINGS

FIG. 1A is an outer view of a foamed polymeric particle containing functional fluid or solid as indicated by reference numeral "10".

FIG. 1B is a cross-section of the particle of FIG. 1A taken along line 1B in FIG. 1A. Part of the particle indicated by reference numeral "10" is the outer surface thereof. Reference numeral "11" indicates one of the pores produced as a result of foaming.

FIG. 2 is a schematic cut-away elevation diagram of the extrusion and pelletizing apparatus useful in carrying out the process of our invention during the operation of said apparatus. Motor 15 drives the extruder screws located at 23A in barrel 16, the extruder being operated at temperatures in the range of about 150° up to about 250° C. At the beginning of the barrel resin at source 12 together with additives, e.g. opacifiers, processing aids, colors, pearlescent agents and densifiers at location 13 is added via addition funnel 14 into the extruder. Simultaneously (when the operation reaches "steady state"), functional fluid or solid is added to the extruder at one, two or more of barrel segments 3–8 of the extruder (which may be a twin screw or single screw extruder) at locations 18a, 18b, 18c and 18d by means of gear pump 23 from source 17. From source 19 into barrel segments 5–10, the gaseous or liquid blowing agents, e.g. nitrogen, carbon dioxide and the like as described supra, are added simultaneously with the addition of the functional fluid or solid. The feed rate range of resin is about 80–300 pounds per hour. The feed rate range of the functional solid or liquid is between 1 and 35% of the feed rate range of the resin. The blowing agent rate range is such that the pressure of the gas or the pressure over the liquid being fed into the extruder is between about 50 and 200 psig. If desired, the extruded ribbon or cylinder may be passed through water bath 20 and pelletizer 21 into collection apparatus 21a. FIG. 22 indicates the travel of the extruded material prior to entering pelletizer 21.

Figure 3:
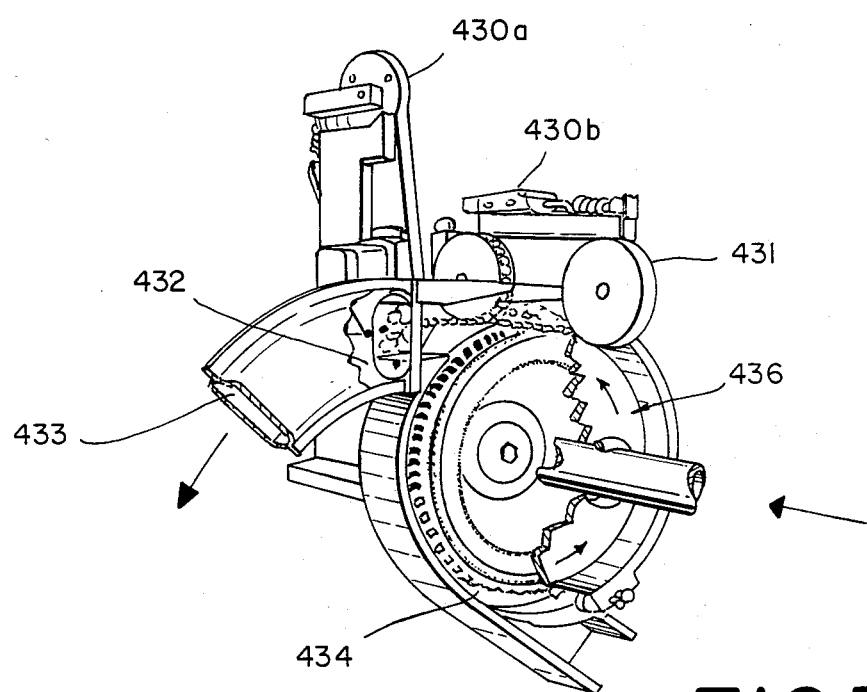
FIG. 3 is a cut-away perspective diagram of a pelletizing apparatus used in conjunction with the extrusion apparatus, for example that illustrated in FIG. 2, whereby the extruded tow is pelletized.

FIG. 3 is a detailed cut-away perspective view of such a pelletizer as is used in conjunction with the apparatus of FIG. 2. The extruded material coming from the water cooler which is already foamed and which already contains functional fluid or solid is fed into the pelletizer at zero pressure at location 434. The pelletizer is operated using a spinning extrusion die 436 and operated by means of a rotating wheel 434. Moving pellet knife 431 and dual knife units 430a and 430b cause pellets to be formed which fly into a cooling water stream 432. The resulting pellets which are foamed and contain functional solid or liquid exit from the pelletizer at 433.

Similarly, an extruded tube which can be used as such or cut into smaller lengths is shown to be formed using the apparatus of FIG. 4. Thus, a single screw 35B taken alone or further together with a second screw 35A makes up part of an extruder in casing 33. Resin from resin funnel 30 is fed in at location 31 into the extrusion barrel upstream from the feeding of functional fluid or solid which is located at source 450. Simultaneously, functional fluid or solid from source 450 is fed through line 460 past valve 461 using pump 462 into the extrusion barrel. The extruder causes an intimate mixing of the functional fluid or solid with the resin in the screw conveyer threads 34 and 36. Simultaneously downstream from the addition point of the functional fluid or solid, gaseous blowing agent is fed through line 43 past valve 42 into the extrusion screws at location 44. The extruded tube then is forced through die 37 and orifice 38 onto conveyer belt 40 in the form of tube 39A which may be subsequently cut at location 39B. The conveyer belt is operated using roller 41.

The resulting extruded foam tubing or foamed pellets may be cut up for the purpose of creation of an article of manufacture which contains a functional fluid or solid. Such article of manufacture may be molded using injection molding apparatus of the type set forth in FIGS. 5A, 5B and 6 or jet molding apparatus of the type set forth in FIG. 7.

Figure 6:
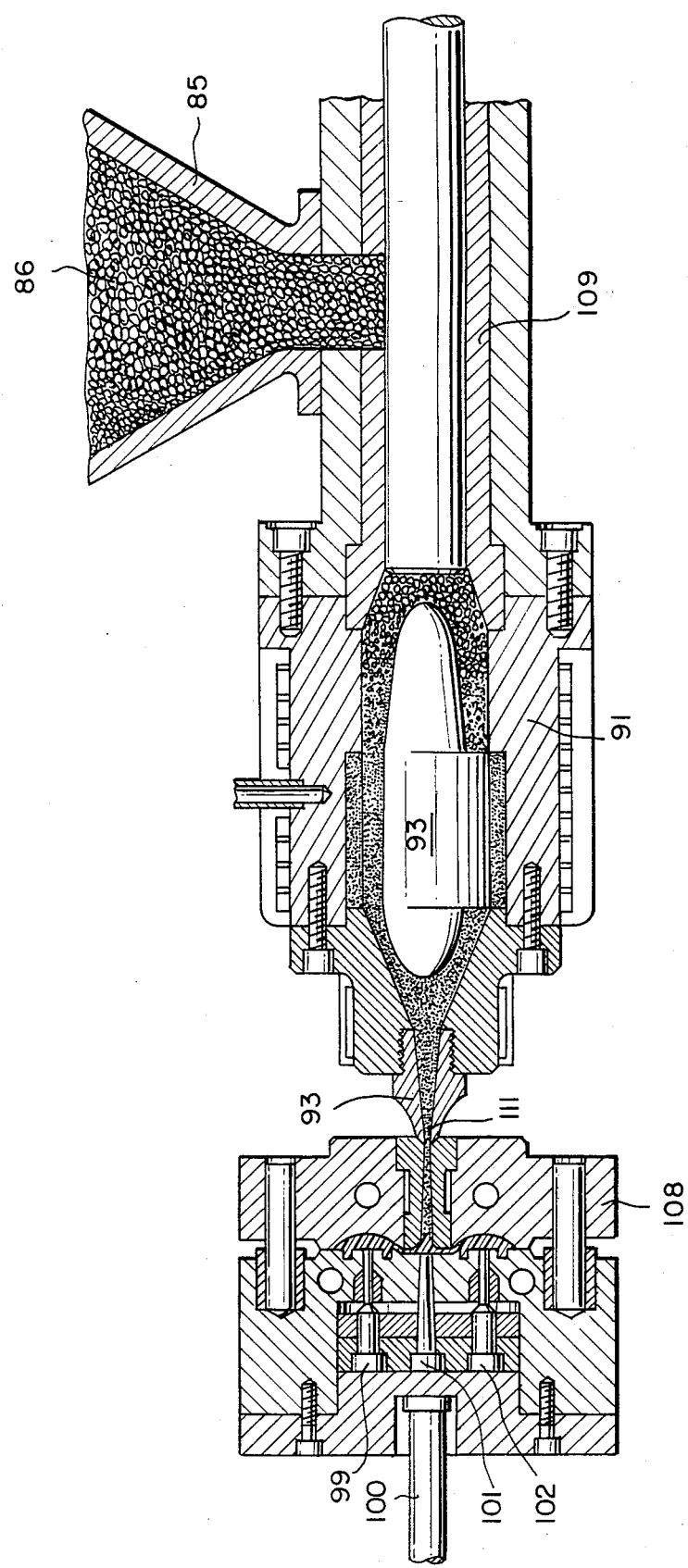
FIG. 6 is a cut-away side elevation view of injection molding apparatus useful in forming articles from the foamed polymeric pellets containing functional fluid or solid produced according to the process of our invention.

FIGS. 5A and 5B show the injection molding apparatus in operation. In FIG. 5A, plunger 73 pushes the foamed functional fluid or solid-containing polymeric particles through cylinder 75 heated by heating unit 76 through die 78 out of orifice 79 into the mold 77/82/80/81. The mold is composed of a male portion 80 and female portion 82. Thus, in summary, the injection molding is characterized by the fact that the molding mix is preheated in a plasticizing cylinder having a cylinder liner 109 (as is shown in FIG. 6) to a temperature high enough for it to retain a quasi-liquid condition and is then forced by plunger 89 through the plunger cylinder into heating cylinder 91 (the temperature for which is measured using a thermocouple in thermocouple container 94), into a closed mold 108 which is cold enough to "freeze" the mixture to a solid sufficiently rigid for ejection. Molding mix containing the foamed polymeric particles 86 is fed into the plasticizing cylinder through hopper 85. When the mold opens, the cylinder plunger 89 moves back permitting material to drop into the cylinder. On the closing stroke, the mold members lock tightly together and the cylinder plunger moves forward forcing the newly delivered material from the hopper into the heating zone of the cylinder 90. This material, in turn, displaces a "shot" of molten material through the nozzle 93 into the mold cavity through orifice 111. The mold is cooled so that the shot hardens quickly. Conditions are controlled so that the molten plastic just has time to reach the outermost recesses of the mold cavity before flow ceases. When the mold is opened, the formed piece is loosened by knockout pins 99, 100 and 101 and 102. The function of the spreader 90 is to spread the mix into thin films and facilitate uniform heating as it passes toward the nozzle 93.

Figure 7:
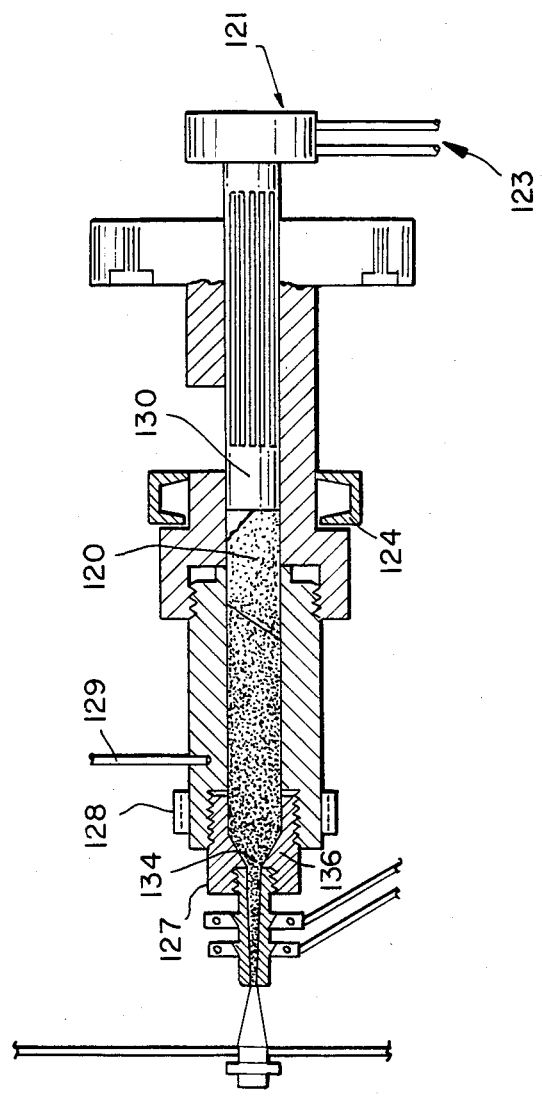
FIG. 7 is a cut-away side elevation schematic view of jet-holding apparatus useful in forming articles of manufacture from the foamed polymeric pellets containing function fluid or solid produced according to the process of our invention.

In FIG. 7 which is a schematic diagram of a cut-away elevation view of a jet molding apparatus useful in producing articles of manufacture using the foamed polymeric functional fluid or solid-containing particles of our invention, the mix 120 is fed into a hopper and from thence falls into a feed cylinder at 120 which is cooled using water cooling 124. The material is then moved forward toward the nozzle end of the cylinder consisting of a nozzle block containing a full taper 127 and heated by a band heater at 128. The amount of heat and rate of heating is measured using a controlling thermocouple 129. The pressure is supplied by the injection plunger 130 having water cooling connection 123 at location 121. As the mix nears the nozzle, mild heat is applied. Temperatures of 150°–200° F. are maintained and the mix is merely warmed in this zone. Under the high pressure of the injection plunger 130, the foamed polymeric functional fluid or solid-containing particles begins to flow into the nozzle 136 at location 134. Thus, for example, placed around the nozzle are two or more electrodes by means of which intense heat is generated by induction. The heat is transferred to the thin stream of mix as it passes through the nozzle 136. By this means, the temperature of the mix is raised almost instantaneously to 400°–500° F. Too high a jet molding temperature can create a destruction of the functional fluid or solid during the production of the functional fluid or solid-containing article of manufacture.

Another feature of our invention is a mass flow control device which can be made into a part of an article utilizing the functional fluid or solid-containing foamed polymers of our invention as is shown in FIGS. 8, 9 and 10. Thus, after placing polymeric foamed functional fluid or solid-containing pellets 167 into cylinder 166 (the pellets, for example, being pellets produced using the apparatus shown in FIGS. 2 and 3), the article which includes mass flow rate accessory 164 with protrusions 163A and 163B is placed into the apparatus shown in FIG. 11 at throat 631. As air or another gas flows through the duct past constriction 631 air is sucked into and through article 166 past openings 162 of the article and 161 of the mass flow rate control device past pellets 167 through openings 162 into the main stream through duct opening 168 into the environment. Protrusions 163A and 163B can be operated laterally at openings 165 in the article of FIGS. 8, 9 and 10 whereby the size of the openings 161 can be varied from "no flow" to "full flow" where the openings 161 precisely coincide with the openings 162.

The operation and full disclosure of the articles of FIGS. 8, 9 and 10 is disclosed in co-pending application for U.S. Ser. No. 377,953 filed on May 13, 1982 (the specification for which is incorporated by reference herein).

FIGS. 11, 12, 13, 14 and 15 illustrate devices containing adjustable Venturi throats resulting from the use of nozzles having adjustable openings used in conjunction with articles which contain the foamed polymeric functional fluid containing polymers of our invention. Examples of variable Venturi throat devices are known in the prior art as set forth in U.S. Pat. No. 1,583,301, U.S. Pat. No. 4,043,772 ("Venturi Scrubber with Variable Area Throat"), U.S. Pat. No. 4,023,942 ("Variable Throat Venturi Scrubber") and U.S. Pat. No. 3,768,234 ("Venturi Scrubber System Including Control of Liquid Flow Responsive to Gas Flow Rate"), the specifications for which are incorporated by reference herein.

Figure 11:
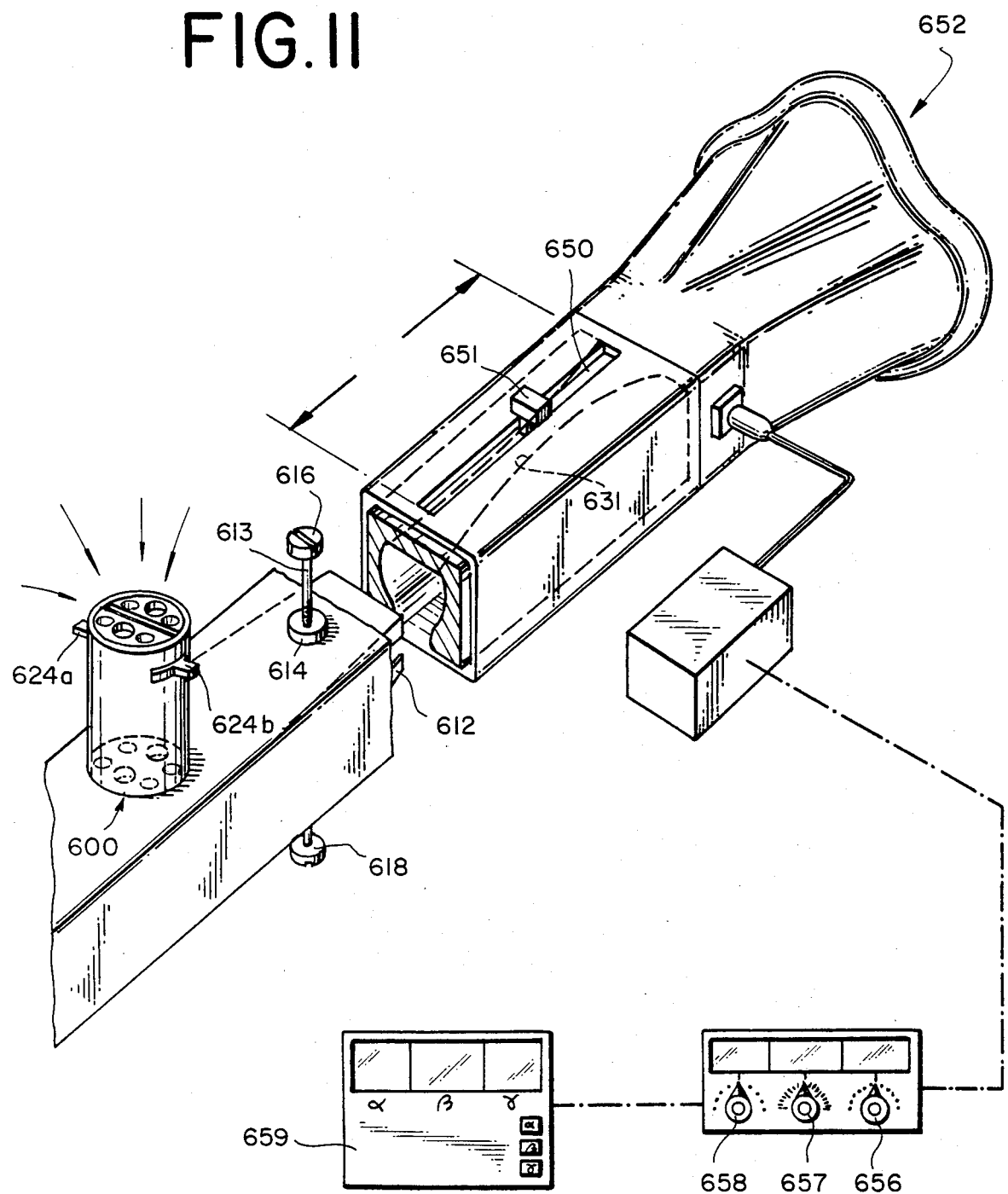
FIG. 11 is a perspective view of apparatus useful in utilizing the functional fluid or solid-containing foamed polymeric particle produced according to the process of our invention having located therein in a detachably affixed fashion an article of manufacture containing the foamed polymeric particle containing functional fluid or solid of our invention and, in addition, an adjustable Venturi nozzle; said apparatus in addition containing a medical diagnostic feature at the front end of said apparatus.

In FIG. 11, a nozzle 612 may be adjusted by bringing closer together or further apart nozzle edges using adjustable screw device 613 fixed via screw threads at 614 to a duct. A main gas stream flows through nozzle 612 adjusted by, for example, adjustment screw 613 via screw caps 616 and 618 past Venturi throat 631. Gas is aspirated through holes in article 600 having a polymer body therein contained which is foamed and contains functional fluid or solid which can be desorbed from the article into the main gas stream flowing through article 600.

The functional fluid-gas stream then travels past location 612 to a mixing point in the proximity of reference numeral "631" to form a mixed functional fluid-gas stream. The gas mass control rate again may be controlled using protrusions 624a and 624b whereby the mass flow rate of aspirated gas may be controlled and slowed down or speeded up as the holes in the article 600 are aligned or malaligned with one another. The apparatus can also include the feature of having the Venturi throat 631 shifted laterally by means of the use of the lateral slot 650 wherein Venturi throat 631 can be shifted laterally along slot 650 using protrusion 651 to move the Venturi throat. An additional feature of the apparatus of FIG. 11 is the inclusion of a human sensory area 652 wherein a person can detect variable aromas and aroma concentrations or the brain can detect various compositions of matter which are volatile and which emanate from article 600. These compositions of matter are useful in diagnosing physiological or psychological malfunctions or aberrations of mammalian species. The person sensing the organoleptic properties evolving from article 600 will then manipulate dials 656, 657 and 658 in device 655 thereby creating readings in device 659 which can be used to aid the diagnosis of various maladies.

Figure 12:
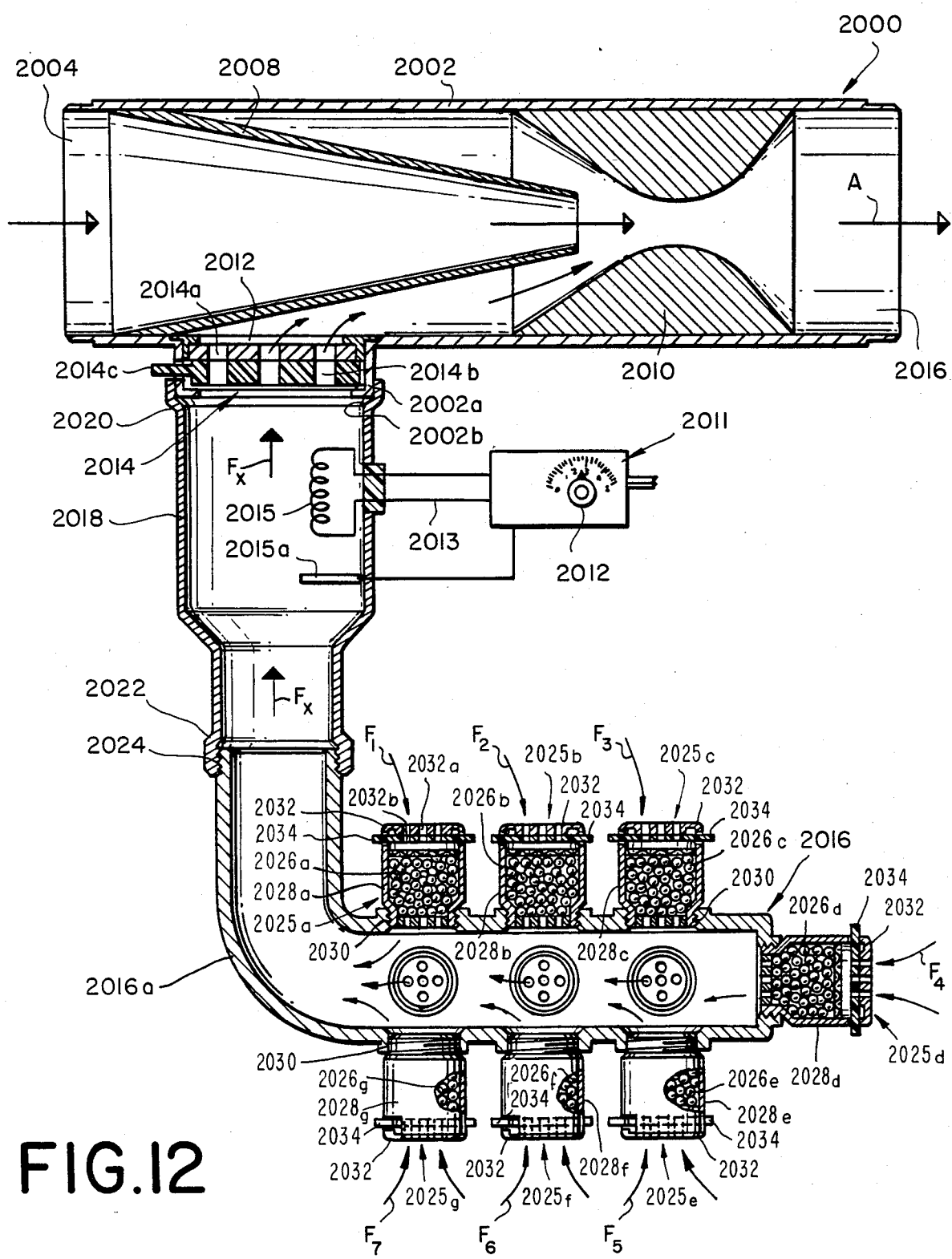
FIG. 12 is a cut-away side elevation view of a section of apparatus useful in employing the foamed polymeric particles containing functional fluid or solid of our invention, said apparatus (i) having detachably affixed thereto a manifold which contains a multiplicity of air passageways which enables air to flow past the polymer particle surfaces and (ii) said manifold having located therein a multiplicity of detachably affixed versions of articles of manufacture containing the foamed polymeric particles which contain functional fluids or solids of our invention.

Referring to FIG. 12 wherein various diagnosing and/or air treatment substances are adsorbed onto foamed polymeric particles, (e.g. polyethylene or copolymers, e.g. polyethylene-polyvinyl acetate) 2018a, 2018b, 2018c and 2018d, these substances may be desorbed in a controlled manner into manifold 2020 and thence through elbow 2016 and duct 2010 past openings 2007 and 2008 into air stream "A". This presupposes that air stream "A" is moving in the direction indicated through the nozzle 2001 past Venturi 2003 having Venturi throat 2002 contained in the main duct 2000. The multiplicity of articles of manufacture of our invention 2017a, 2017b, 2017c, 2017d, 2017e, 2017f, 2017g, 2017h, 2017k, 2017m and other articles of manufacture which may be detachably affixed at, for example, 2019a to manifold 2020 may be manipulated whereby air streams "$F_1$", "$F_2$", "$F_3$", "$F_4$", "$F_5$", "$F_6$" and "$F_7$"et al. may be varied insofar as their mass flow rates are concerned past the foamed functional fluid-containing polymeric particles of our invention being indicated by reference numerals "2019a", "2019b", "2019c", "2019d" . . . "2019m". Each of these air streams "$F_1$", "$F_2$", "$F_3$", "$F_4$", "$F_5$", "$F_6$", "$F_7$", et seq. may be controlled by varying the variable openings 2023a, 2023b, 2023c, 2023d, et seq. using the variable opening device 2022a, 2022b, 2022c, et seq. In addition, the overall flow of mixed functional/diagnostic gas passing through openings 2007 and 2008 may be varied using control lever 2004 whereby the openings 2007 and 2008 may be offset from "full flow" to "no flow".

Still another important feature of the utilization of the present invention is illustrated in FIG. 12 wherein a multiple manifold carrying a plurality of articles of manufacture may be used for diagnosing and/or treating the air with pleasant aromas and/or pheremones and/or air fresheners and/or insect repellents and/or animal repellents is illustrated.

It is apparent that the apparatus 2000 illustrated in FIG. 12 comprises an elongated air duct 2002 having an air inlet 2004 and an air outlet 2006. The elongated air duct 2002 includes a nozzle 2008 and a Venturi throat 2010 which constitutes the aspirating mixing system of the present invention. Furthermore, the air duct 2002 includes an opening 2012 wherein a flow control device 2014 is conveniently arranged to control the overall flow of functional fluid passing therethrough.

A multiple manifold 2016 is operative by means of a connection to the elongated air duct 2002 through a duct 2018 having one end 2020 welded to a collar 2002a which is an integral part of the duct 2002 and provides a seat 2002b for the flow control device 2014. The opposite end 2022 of duct 2018 includes a male threaded portion 2024 capable of being connected to the open end of an elbow 2016a. It will be appreciated by the above construction that elbow 2016a constitutes an important part of the multiple manifold 2016 since it carries a multiplicity of articles of manufacture 2025a, 2025b, 2025c, 2025d, 2025e, 2025f and 2025g which may be detachably affixed thereon. These articles of manufacture may contain various diagnosing and/or air treatment substances imbedded into or adsorbed on the foamed polymeric functional fluid-containing particles 2026a, 2026b, . . . 2026g housed in cartridges 2028a, 2028b, 2028c . . . 2028g detachably connected to a threaded portion 2030 of elbow 2016. Each article of manufacture 2025a, 2025b, 2025c . . . 2025g, etc. may include an air flow control cap 2032 for controlling air streams "$F_1$", "$F_2$", "$F_3$", "$F_4$", "$F_5$", "$F_6$", "$F_7$", etc. in a controllable manner passing through each individual cartridge by varying the variable openings 2032a and 2032b of the flow control cap 2032 through a control lever 2034. Each control lever 2034 may be manipulated whereby air streams "$F_1$", "$F_2$", . . . "$F_7$", etc. may be varied insofar as their mass flow rates are concerned past the foamed polymeric particles containing functional and/or diagnostic substances adsorbed thereon or dissolved therein.

However, the overall flow of mixed functional/diagnostic gas passing into air duct 2002 to be mixed with the air stream "A" moving in the direction indicated through the nozzle 2008 and Venturi throat 2010, may be varied using the flow control device 2014 whereby openings 2014a and 2014b may be offset from full flow to no flow through a control lever 2014c.

The gas stream "$F_x$" which is the sum of the air streams "$F_1$", "$F_2$", $F_3$", "$F_4$", "$F_5$", "$F_6$", "$F_7$", et seq. and the sum of the mass flow rates of functional and/or diagnostic fluid being desorbed from foamed polymer particles 2026a, 2026b, et seq., "$F_{p1}$", "$F_{p2}$", "$F_{p3}$" et seq. is shown by the equation:

$$\Sigma[F_n + F_{pn}] = F_x$$

wherein "$F_n$" is the flow rate of the air through the articles of manufacture of our invention 2025a, 2025b, 2025c, et seq. and the flow rate of the desorbed functional/diagnostic fluid from the foamed polymeric particles in the articles of manufacture of our invention "$F_{p1}$", "$F_{p2}$", "$F_{p3}$" et seq. Thus, "$F_n$" is defined according to the equation:

$$\sum_{1}^{ni} [F_1 + F_2 + \ldots + F_{ni}] = F_n$$

and "$F_{pn}$" is defined according to the equation:

$$\sum_{p1}^{pni} [F_{p1} + F_{p2} + \ldots + F_{pni}] = F_{pn}$$

The flow of the functional fluid combined with the aspirated air "$F_1$", "$F_2$", "$F_3$", "$F_4$", "$F_5$" is shown as "$F_x$" and joins the main gas stream "A" at Venturi throat 2010 whereby the sum total of gas streams evolving at 2006 from duct 2002 is shown as "Q" or "$F_x + A$" thusly:

$$\Sigma[F_x + A] = Q$$

The temperature of stream "$F_x$" may be controlled using heating means 2011 having a control device 2012 which may be manually or automatically controlled by means of an electronic program controller. The control line 2013 is operatively connected to a heating device 2015 which may be continuous or intermittent operatively connected to a temperature sensing device 2015a which may be connected via thermostat to said heating means 2011.

Figure 14:
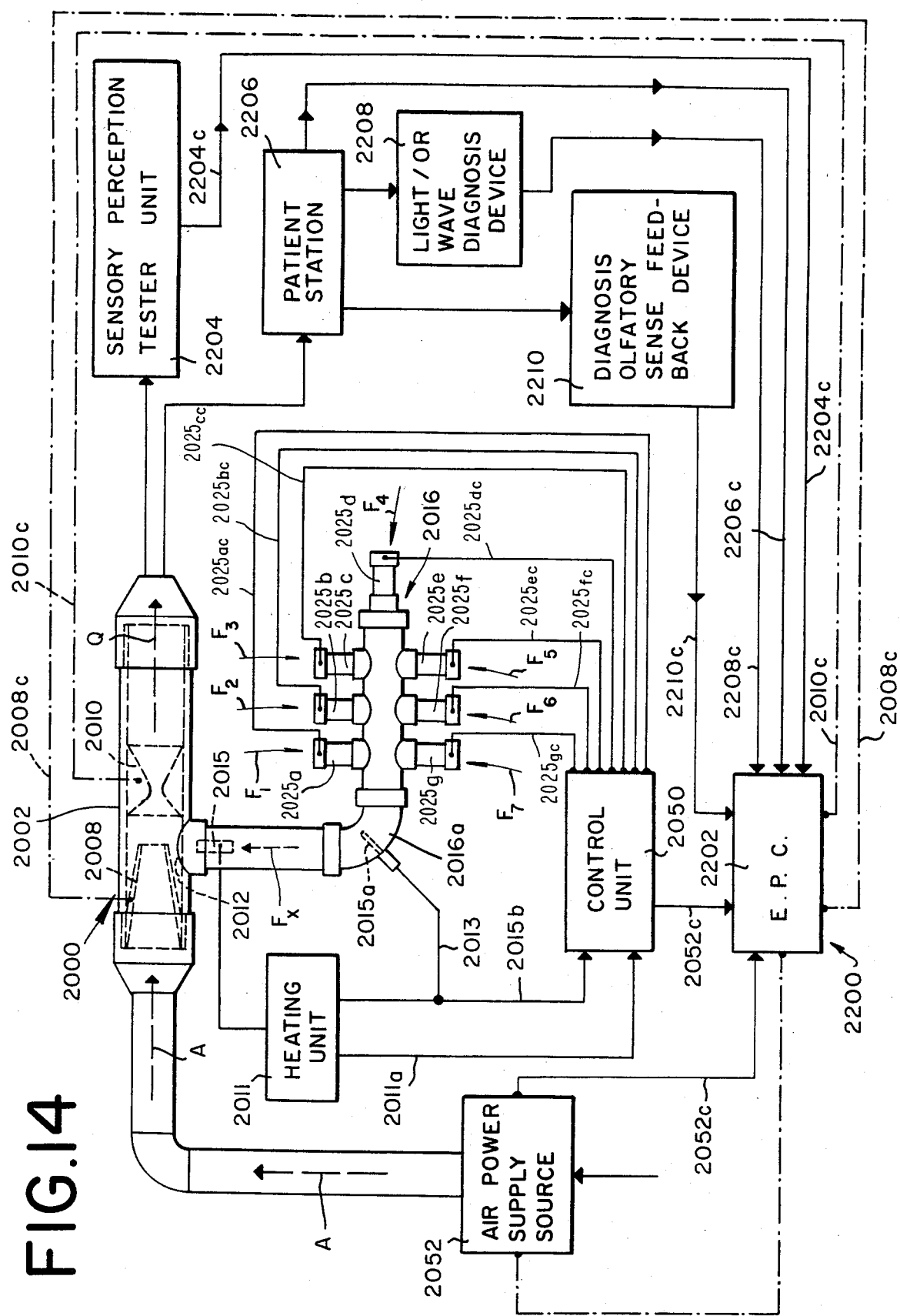
FIG. 14 is an exploded perspective view of the apparatus shown in FIG. 13 wherein a number of elements of said apparatus which are capable of creating a variation in the output of said apparatus are shown to be interconnected with an electronic program controller.

The input of air streams "$F_1$", "$F_2$", "$F_3$", "$F_4$", "$F_5$", "$F_6$" et seq. into manifold 2016 may also be controlled using an electronic program controller as will be seen by an examination of FIG. 14 infra.

The apparatus of FIG. 12 can be used as an air freshening device or a medical diagnostic device or an olfactory testing device, for example, a device useful in testing the olfactory senses of prospective perfumers or flavorists in the perfume and flavor industry. The device can also be used to devise novel fragrance formulations whereby the tester detects the aromas evolving at 2006, the tester or individual being diagnosed for medical diagnoses located at location 2040 as shown in FIG. 13.

Figure 13:
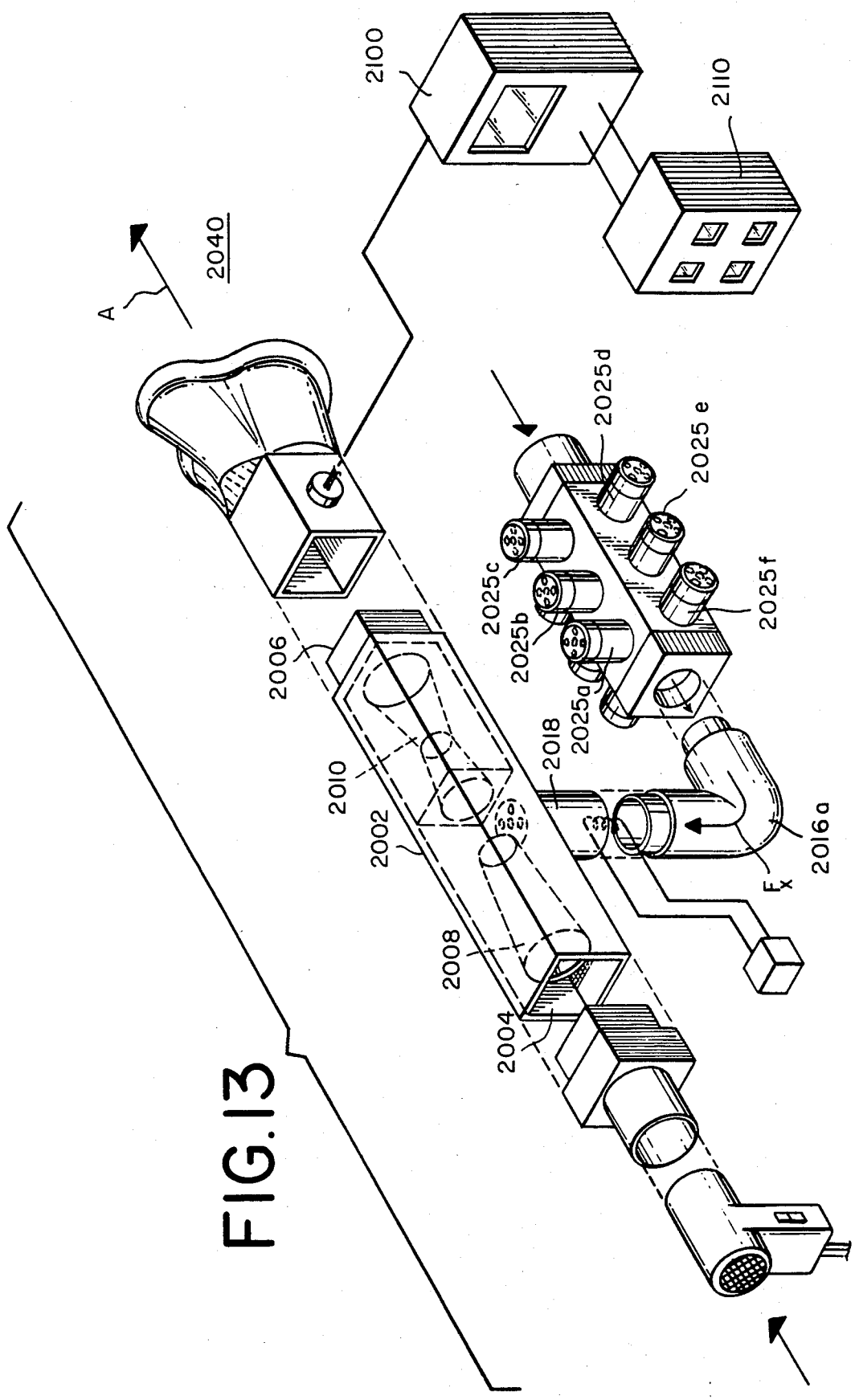
FIG. 13 is an exploded perspective view of an embodiment of the apparatus capable of utilizing the foamed polymer particles containing functional fluid or solid of our invention whereby said apparatus is in the form of a medical diagnostic device.

FIG. 13 is a perspective partially exploded view of a preferred embodiment of the apparatus useful in using our invention including a tester or patient (being diagnosed) input device 2100 operatively connected to a manual monitor/recorder 2110 which will indicate the sensory perception of the tester or individual being diagnosed. In place of the manual device 2100, a device known in the art for measuring brain wave patterns may be applied at this location (not shown). Thus, for example, such a device may be a PETT brain scan which, for example, shows in a normal person, symmetrical metabolism of $^{11}$C-2-deoxyglucose in the temporal lobes, a comparable metabolic rate in the frontal area and a considerable increased metabolic rate in the visual cortex as a result of stimulation resulting from the diagnosing gas. Such a scan is illustrated in the 1981 annual report of International Flavors & Fragrances Inc. published by International Flavors & Fragrances Inc. in 1982. Said annual report is incorporated by reference herein.

The mass flow rate "Q" at location 2040 which is defined according to the equation:

$$\Sigma[F_x+A]=Q$$

wherein $F_x$ is defined according to the equation:

$$\Sigma[F_n+F_{pn}]=F_x$$

may be further broken down because the density of the desorbing gasses "$F_1$", "$F_2$", "$F_3$", "$F_4$", "$F_5$", and the density of the functional fluid or diagnosing fluid or testing fluid "$F_{p1}$", "$F_{p2}$", "$F_{p3}$" et seq. are shown, respectively, by the symbols:

$$\rho_o \text{ and } \rho_i$$

The equations governing the mass flow rate of these fluids are shown thusly:

$$F_{ni}=\rho_o[T,P]\cdot S_{ni}\cdot u_{ni}$$

and $$F_{pni}=\rho_i[T,P,s]\cdot S_{pni}\cdot u_{pni}[u_{ni}-F_{ni}\cdot D_{pnsi}]$$

If time is shown by the term:

$$\theta$$

then the reaction of the individual being diagnosed at location 2040 may be shown according to one or more of the following partial or total derivatives, to wit:

$$\frac{\partial F_{ni}}{\partial \theta}; \frac{\partial F_{ni}}{\partial F_{pni}}; \frac{\partial^2 F_{ni}}{\partial \theta \, \partial F_{pni}};$$

$$\frac{\partial F_{pni}}{\partial F_{ni}}; \frac{d^2 F_{ni}}{d^2\theta}; \frac{\partial^2 F_{pni}}{\partial F_{nii} \, \partial F_{nij}};$$

$$\frac{\partial F_{nii}}{\partial F_{nij}}$$

wherein "$F_{nii}$" is a flow of gas "$F_1$", "$F_2$", "$F_3$", "$F_4$", et seq. different from the flow of gas "$F_1$", "$F_2$", "$F_3$", "$F_4$", "$F_{nij}$". In the foregoing equation "$U_{ni}$" is the linear velocity of the stream "$F_1$", "$F_2$", "$F_3$", "$F_4$" et seq. and "$S_{ni}$" is the area of flow in the article of manufacture useful in conjunction with our invention 2025a, 2025b, 2025c, et seq.

The flow of olfactory sense testing fluid or diagnosing fluid or other functional fluid as shown by "$F_{p1}$", "$F_{p2}$", "$F_{p3}$", et seq. or in general "$F_{pni}$", is shown according to the equation:

$$F_{pni}=\rho_i[T,P,s]\cdot S_{pni}\cdot u_{pni}[u_{ni}-F_{ni}\cdot D_{pnsi}]$$

wherein "T" and "P" represent, respectively, temperature and pressure of the gas and wherein "s" represents the surface area of the polymeric particles having adsorbed therein a functional substance, e.g. 2026a, 2026b, 2026c et seq. and wherein "$D_{pnsi}$" represents the diffusivity of the functional fluid or solid and/or diagnostic fluid or solid and/or testing fluid or solid in each of the foamed polymeric particles for each of the sets of particles 2026a, 2026b, 2026c, et seq.

In general, the mass flow rate of the fluid in manifold 2016 is shown by the equation:

$$F=\rho S u$$

where the symbol:

$$\rho$$

is the density of the fluid, "S" is the mean cross-sectional area of flow of the fluid and "u" is the linear velocity of the fluid. The flow of the fluid is further defined according to the differential equation:

$$\frac{\partial F}{\partial G} = Su\frac{\partial \rho}{\partial G} + \rho S\frac{\partial u}{\partial G} + \rho u \frac{\partial S}{\partial G}$$

where "G" represents any of the variables "$F_{ni}$", "$F_{pni}$", "$F_{nij}$", "$F_{nijp}$", "T", "P", "$\theta$" and the like. If "H" is a variable of flow different from "G", the mass flow rate is definable according to the equation:

$$\frac{\partial^2 F}{\partial G \, \partial H} = Su\frac{\partial^2 \rho}{\partial G \, \partial H} + \rho S\frac{\partial^2 u}{\partial G \, \partial H} + \rho u \frac{\partial^2 S}{\partial G \, \partial H} + \cdots$$

which is a generalized form of partial differential equation showing the interrelationship of all variables involved in the flow.

FIG. 14 is a schematic diagram of another embodiment of the apparatus shown in FIGS. 12 and 13 including an electronic program control system 2200 operative by association with the multiple manifold for controlling electronically the flow rates of air streams which evolve into flow rate "Q" which may be used (i) for testing the olfactory senses of prospective perfumers or florists; (ii) for devising and detecting novel fragrance formulations; (iii) for medical diagnoses whereby a patient is being diagnosed using an electronic program controller or computer such as, for example, using a PETT scan as illustrated in the International Flavors & Fragrances Inc. 1981 annual report.

Thus, the electronic program control system 2200 includes a programmer computer 2202, a sensory perception testing unit 2204 for testing different mixtures of substances, a patient testing unit or station 2206 whereat a patient may be diagnosed manually or by means of a light or wave means diagnosis device 2208. Furthermore, the patient may be diagnosed at 2206 electronically through a diagnosis olfactory sense feed-back device 2210 plugged into the programmer computer 2202.

More specifically, in the operation of the apparatus of FIG. 14, the patient, for example, at location 2040 or station 2206 senses air stream operating at flow rate "Q" which combines the streams entering cartridges 2025a, 2025b, 2025c, 2025d, 2025e . . . 2025g evolving from orifice 2012 and heated to various temperatures using heating means 2011 controlled by the control device 2011 operatively connected to a temperature sensor 2015a through control line 2013. The air streams "$F_1$", "$F_2$", "$F_3$" et seq. mix with the air stream "A" from blower 2042 through duct 2002. Gas stream "A" passes through nozzle 2008 past Venturi throat (which may be variable) 2010. In addition, the position of the Venturi throat 2010 may be varied and the diameter of the Venturi may be varied using electronic programmer control lines 2008c and 2010c.

The diagnosis-olfactory sense feedback device 2210 is operatively connected to the electronic programmer 2202 via line 2210c. The tester or patient sense device 2202 which may be measuring brain waves and brain wave patterns is operatively connected with an electronic program controller device 2100 via control line 2202c. A sensory perception tester unit 2204 is operatively connected to the electronic program controller 2202 via line 2204a wherein intermittently or continuously the mixture of testing substances or olfactory sensing substances in article of manufacture 2025a, 2025b, 2025c, 2025d, 2025e . . . 2025g et seq. are varied through a control unit 2050 which is operatively connected to the program computer 2202 via line 2050c whereby variation of flow rate will depend upon the output of diagnosis sense feedback device 2210 or tester or patient sensory feedback device 2204 via control lines 2025ac, 2025bc, 2025cc, 2025dc, 2025ec, 2025fc, 2025gc and the like and through main control line 2017xc. In addition, the main flow rate "$F_x$" from manifold 2016 through orifices 2014a and 2014b may be controlled via optional control lines as well as an optional control line which controls the nozzle diameter by means of an electro-mechanical mechanism (not shown) plugged into the electronic program controller 2202.

The control unit 2050 controls the operation of heating unit 2011 and temperature sensor 2015a through lines 2011a and 2015b. An air power supply source 2052 is operatively connected to the programmer computer 2202 via line 2052c whereby air supply to air duct 2002 may be controlled electronically in accordance with the air flow required.

Optionally, the apparatus of FIG. 14 can also involve the use of light or other wave diagnosis devices 2208 plugged into the electron program controller 2202 via control line 2208c. The involvement of detection of various wavelengths of light in conjunction with various olfactory perceptions by the individual at location 2040 can give rise to an even more accurate determination of physiological and/or neurological functions or malfunctions and therefore give rise to a more accurate diagnosis.

Figure 15:
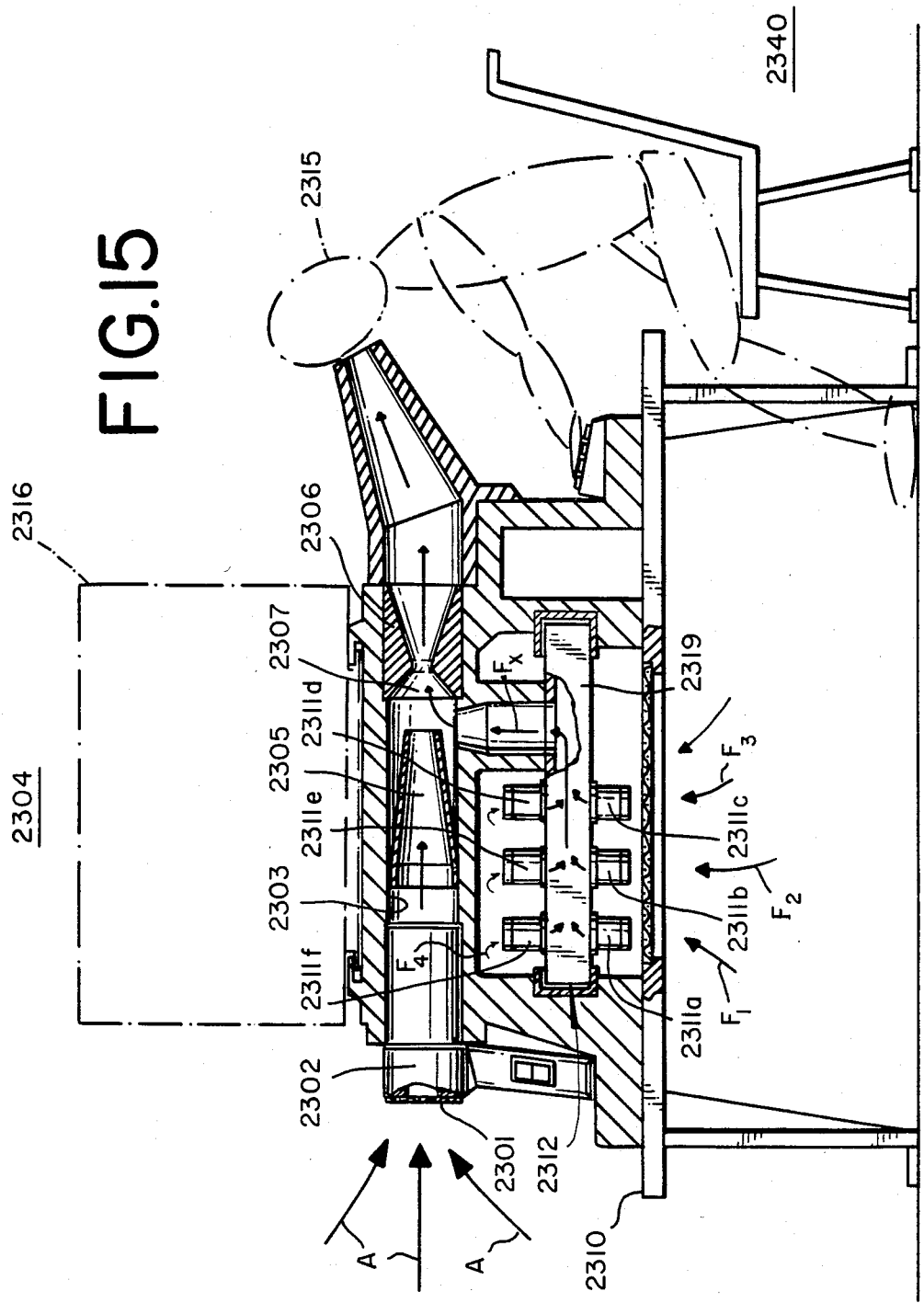
FIG. 15 is a cut-away side elevation view of a section of medical diagnosis and/or sensory perception apparatus useful in employing the foamed polymer particles containing functional fluid or solid of our invention.

Another version of the olfactory testing and/or physiological malfunction diagnosing apparatus which uses the articles of manufacture of our invention is set forth in FIG. 15.

Now referring to FIG. 15, air at main air flow rate "A" is sucked into conduit 2303 by means of blower 2302 through screen 2301. The apparatus resting on table 2310 is either operated manually or via an electronic program controller involving patient 2315 at location 2340. The air at flow rate "A" blown using blower 2302 proceeds through duct 2340 and nozzle 2305 which may be varied using an electronic program controller plugged into a console or brain wave sensing device 2316. The air at flow rate "A" combines with functional fluid/aspirated air at flow rate "$F_x$" at Venturi throat 2307 of the Venturi 2306 which may be movably connected to conduit 2303. The air or other aspirating gas at flow rates "$F_1$", "$F_2$", "$F_3$", "$F_4$", et seq. proceeds through an article of manufacture useful in conjunction with our invention containing foamed polymeric particles having functional and/or diagnosing and/or testing fluid adsorbed or dissolved therein 2311a, 2311b, 2311c, 2311d, 2311e, et seq. into manifold unit 2312 which may be removed from the apparatus in order to quickly and conveniently replace cartridges 2311a, 2311b, 2311c, 2311d and 2311e, et seq. The manifold unit 2312 may be rotated about rotating cylinder 2309 in order for efficient removal manually or mechanically by either the individual being tested for physiological malfunctions or being olfactory tested at location 2340 or by a professional operator who is also monitoring the brain wave functions at another location behind console 2316 at location 2304.

Another article useful in conjunction with the foamed functional fluid or solid polymeric particles or articles of manufacture of our invention comprises an ellipsoidally-shaped detergent tablet 230 containing a solid plastic core 232 which is fabricated from foamed polymeric functional fluid or solid-containing particles or articles of manufacture (e.g. containing polyethylene, polypropylene, nylon or the like) having therein, for example, microvoids from which a functional fluid or solid such as an aromatizing substance, e.g. a perfume material, will be controllably transported from the plastic core into and through the soap cake over a reasonable period of time during the use of the soap cake. Such foamed polymers can be polymers such as those described in U.S. Pat. No. 4,247,498 issued on Jan. 27, 1981, the specification for which is incorporated by reference herein. Surrounding the central plastic core containing functional fluid or functional solid such as perfume material 232 is detergent 230' which is in the solid phase at ambient condition, e g. room temperature, and atmospheric pressure. Examples of workable detergents 230' are "elastic" detergents such as those described in U.S. Pat. No. 4,181,632 issued on Jan. 1, 1980, the disclosure of which is incorporated by reference herein, or "transparent" soaps such as those set forth in U.S. Pat. No. 4,165,293 issued on Aug. 21, 1979, the disclosure of which is incorporated herein by reference. Examples of the detergent 230' useful in our invention are those set forth as "variegated soaps" in Canadian Letters Pat. No. 1,101,165 issued on May 19, 1981, the disclosure of which is incorporated by reference herein.

On use of the soap tablet 230 or detergent bar, the aromatizing agent or other functional fluid or solid originally located in the plastic core 232 is transported at a steady state from core 232 through core surface 231 through the detergent 230' and finally through the surface of the detergent bar at, for example, 233, 234, 235 and 236.

The detergent bar or tablet 230 of our invention may be of any geometric shape, for example, a rectangular parallelepiped tablet 230a is shown in FIGS. 20, 21 and 22 containing solid plastic core 239 (fabricated from the foamed polymeric particles of our invention). The functional fluid or solid, e.g. aromatizing material, located in solid plastic core 239 on use of the detergent bar passes through, at steady state, surface 237, detergent 238 and finally, surface 239 at, for example, locations 240, 241, 242 and 243. The environment surrounding the detergent bar, on use thereof, is then aesthetically aromatized at 243, 244 and 245, for example, when the functional fluid is an aromatizing material.

As is shown in FIGS. 23, 24 and 25, the plastic core of the detergent tablet 230 may have a single finite void at its center 251 in which a functional fluid such as an aromatizing agent is contained. The plastic core then is a shell 248 having outer surface 252. The functional fluid, e.g., aromatizing agent contained in the void in the plastic core permeates through the shell 248, past surface 252 at a steady state, through the detergent 247 and to the environment at, for example, 256, 257, 258 and 259.

In addition to the functional fluid, e.g., aromatizing agent contained in the core, e.g., core 239 or core void 249, the core can also contain other materials for therapeutic use, for example, bacteriastats, deodorizing agents other than the original functional fluid, e.g., aromatizing agent already contained in the core, and in addition, or in the alternative, insect repellents, shark repellents, animal repellents and the like.

In the alternative, the plastic core of the detergent tablet of FIGS. 23, 24 and 25 may have an empty single finite void at its center with the functional fluid, e.g., aromatizing agent contained in the shell 248.

At the end of the use of the detergent tablet, the hollow core or the solid core can be used as an aroma-imparting air freshener or insect or animal repellent-type household article. In addition, depending upon the ratio of the volume of the void 251, the detergent tablet of FIGS. 23, 24 and 25 can be so fabricated that it will float on the surface of the liquid in which it is being used and this physical attribute has certain obvious advantages, e.g. as a "toy" or as a "marker" in a natural body of water.

Figure 26:
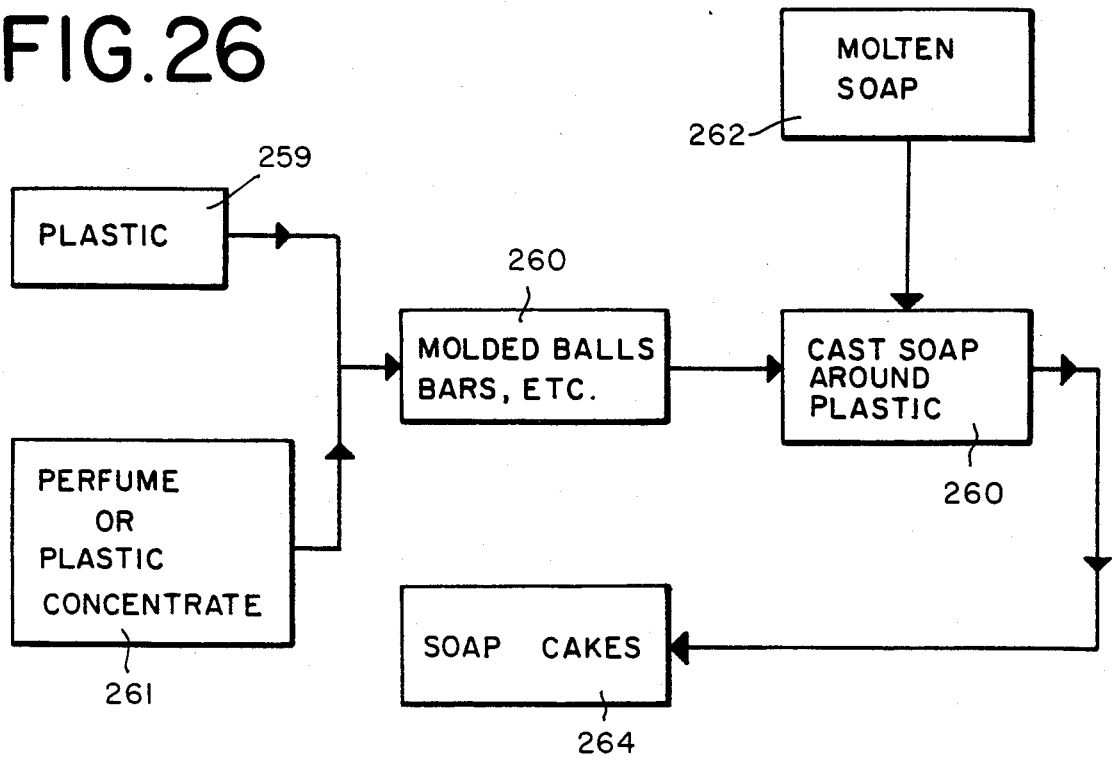
FIG. 26 is a flow chart of a process used in conjunction with our invention for forming soap cakes containing aromatized cores which include fused aromatized polymeric particles.
Figure 27:
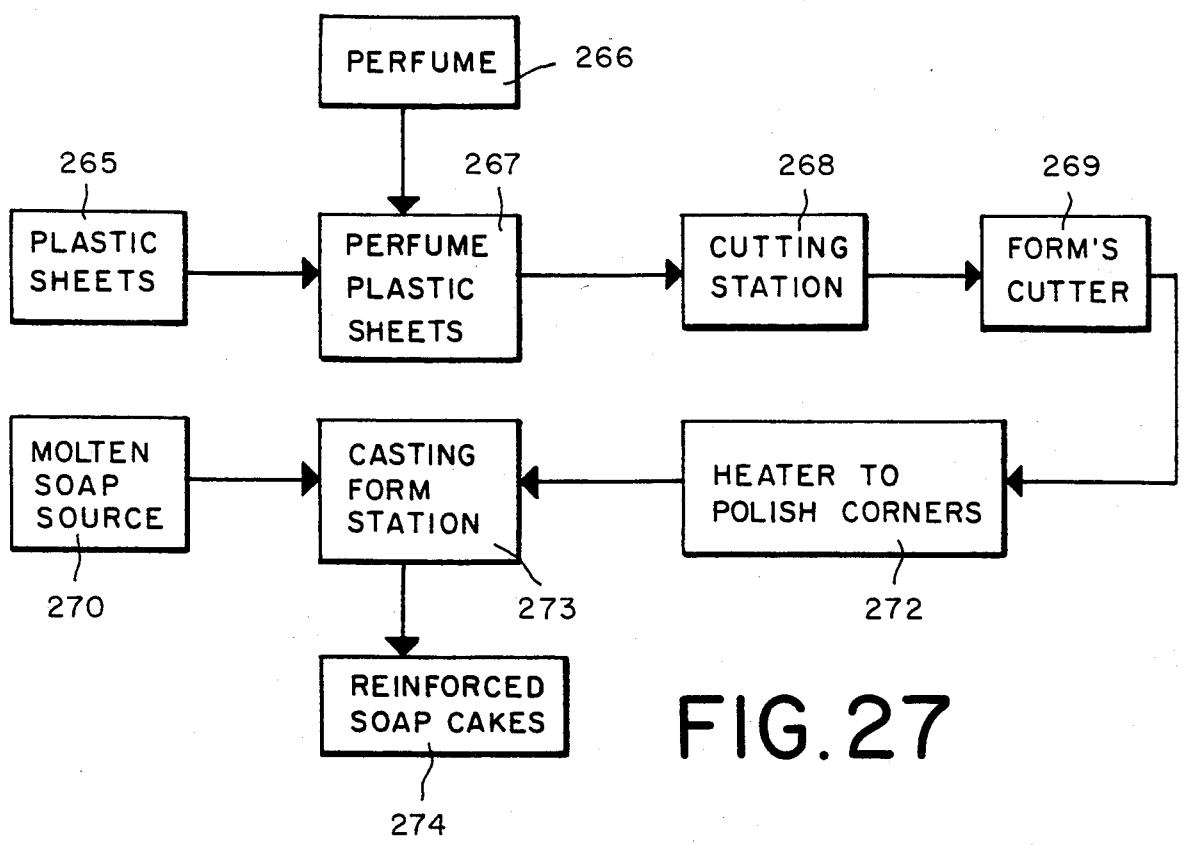
FIG. 27 is another flow chart of a process used in conjunction with the aromatized polymer or functional fluid containing fused polymeric particles of our invention for formulating reinforced soap cakes containing aromatized solid cores containing fused polymeric particles or hollow cores containing fused polymeric particles of our invention.

FIGS. 26 and 27 set forth in block diagram form process flow sheets for preparing the detergent tablets within which are contained the cores fabricated from the foamed polymeric particles or articles of manufacture produced in accordance with the process of our invention.

Thus, in FIG. 26, a perfume or "concentrate of perfume in polymer" 261 is combined with additional polymer 259 (which may be additional foamed polymeric particles or other polymer, e.g. polyethylene or copolymer) and the resulting mixture is molded into bars, ellipsoids, rectangular parallelepipeds or spheres at 260. Soap is then cast around these molded polymer spheres, ellipsoids or rectangular parallelepipeds at 263 from a source of molten soap 262. The resultant castings are then cooled in order to form soap cakes in the solid phase at ambient conditions at 264.

In the alternative, polymer sheets 265 are imbedded with functional fluid, e.g., aromatizing agent from source 266 to form aromatized plastic sheets at 267. These aromatized plastic sheets are then cut at the cutting station 268 to form cut forms at 269 which are then heated to such a temperature whereby the angular sharp corners are "polished" at 272. Soap from molten soap source 270 is then cast around the resultant plastic forms at casting station 273 and the resultant material is then cooled thereby forming reinforced aromatized soap cakes at 274.

Figure 28:
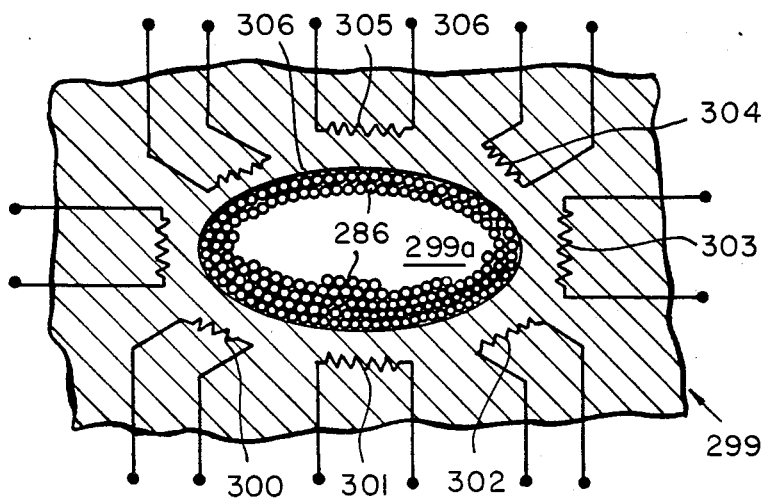
FIG. 28 is a fragmentary top plan view of the heated platen showing the configuration of dish-cup-like portions of the platen wherein the aromatized fused foamed polymeric pellets (which may or may not include other aromatized or nonaromatized polymers) are compressed into plastic cores for incorporation into detergent tablets.
Figure 29:
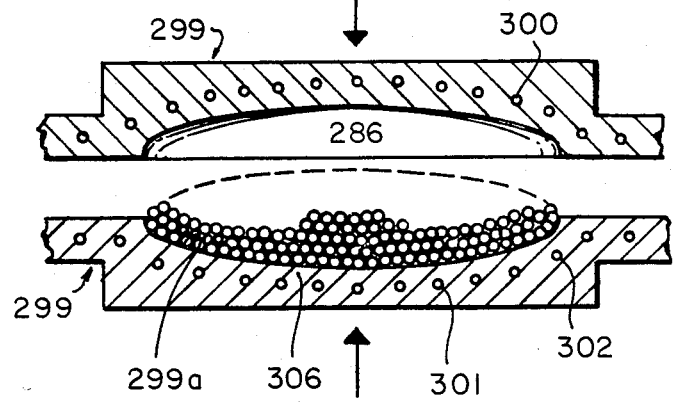
FIG. 29 is a fragmentary side elevational view with parts broken away and showing in section the heated platens of the apparatus of FIG. 28 during the compression step of the process of making cores of aromatized foamed polymeric particles for the soap tablets used in conjunction with the present invention.
Figure 30:
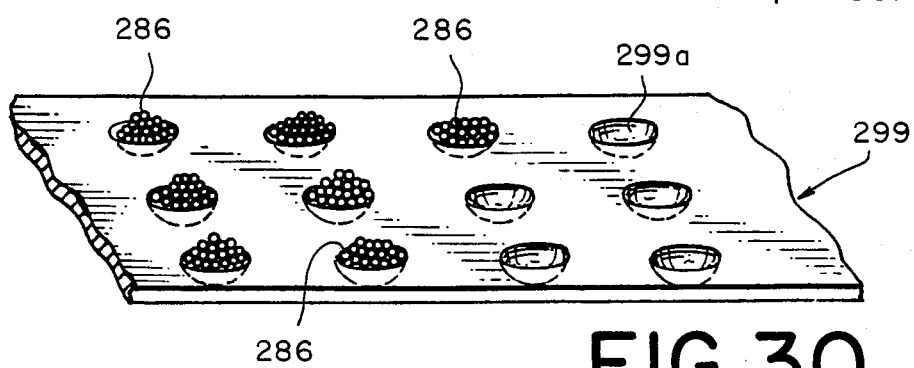
FIG. 30 is a perspective view of a heated platen part of the apparatus containing ellipsoidal voids containing therein aromatized foamed polymeric pellets ready for compression.
Figure 31:
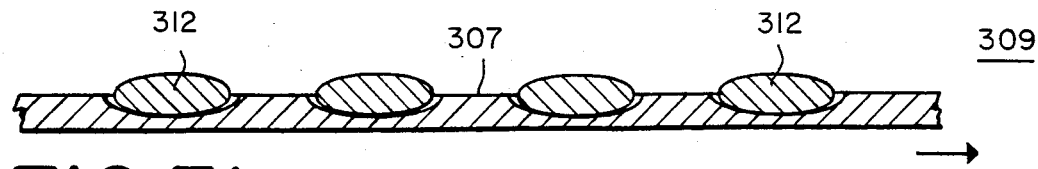
FIG. 31 is a schematic view of the heated platen of FIG. 30 after the compression step of compressing the aromatized foamed polymeric pellets into aromatized plastic cores.

As will be seen in FIG. 28, pellets of foamed polymeric particle or other article of manufacture 286 are placed, for example, into cup-like portions 299a of platens 299 heated with heating element 300, 301, 302, 303, 304 and 305 which convey heat to surfaces 306. The platens 299 are moved together after the pellets 286 are placed therein squeezing them together and heating them so that they fuse into the plastic cores suitable for the production of the soap or detergent tablets useful in conjunction with the foamed polymeric particles or other articles of manufacture of our invention which also contain functional fluids or solids.

The number of pellets 286 placed onto surfaces 306 and the pressure exerted by platens 299 causes the flow of plastic between pellets 286 whereby the functional fluid or solid, e.g. scenting or aromatizing material, does not escape substantially from the pellets. This requires a high pressure of 100–5,000 atmospheres and the maintenance of a relatively low temperature for fusing, between 30° F. and 70° F., for example.

The fused cores 312 after compression of the pellets 286 (so that they flow together at surfaces 307) are releasable from the platens at 309 and usable in the processes set forth infra. It is convenient to incorporate in the polymer particles prior to extrusion and prior to foaming, a small amount of mold releasing agent well known to be useful in such processes.

Figure 32:
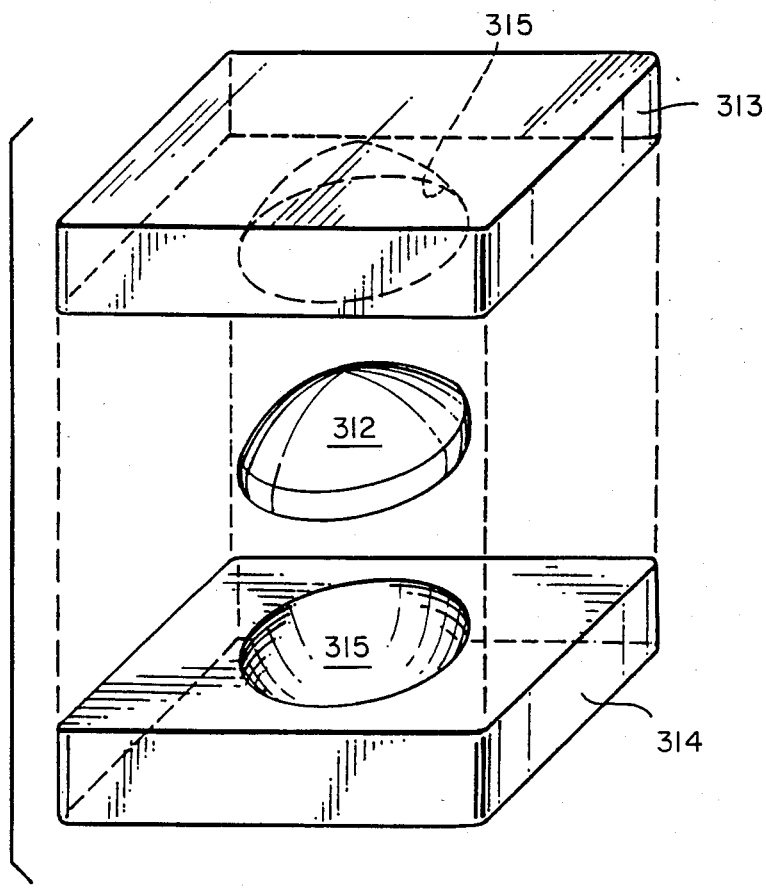
FIG. 32 is a perspective view of a technique for inclusion of an aromatized core containing compressed foamed polymeric pellets produced according to the process of our invention into a detergent tablet using an upper detergent tablet section and a lower detergent tablet section.

The thus fused core 312 as is shown in FIG. 32 may then be incorporated between two tablet portions of soap or detergent 313 and 314, the upper tablet being 313 and the lower tablet being 314. Voids 315 are provided in upper tablet 313 and lower tablet 314 whereby when they are placed onto core 312 simultaneously and whereby when they are fused together by means of application of an exterior source of heat, the core 312 will conveniently fit snugly between the upper tablet 313 and the lower tablet 314.

Figure 33:
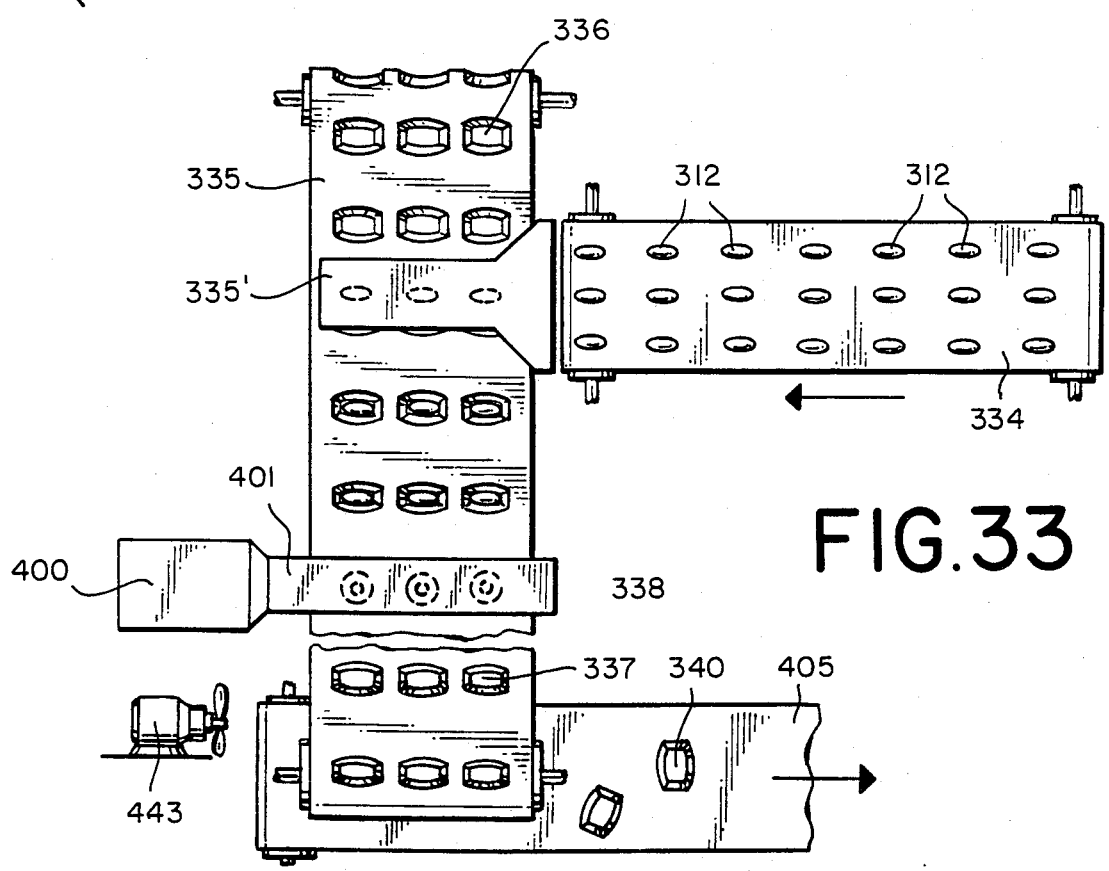
FIG. 33 is a top plan view of an alternative embodiment of the apparatus for preparing molded detergent tablets around aromatized cores formed from foamed polymeric aroma-containing pellets produced according to the process of our invention.

In the alternative, the cores 312 as is illustrated by FIG. 33, may be passed onto conveyor belt 334 into cups 336 on conveyor belt 335 through a distributing hopper 335'. Cups 336 are then filled from filler 338 with molten soap maintained at a fluid temperature by heater 400 at location 401. At location 402 the cores now located in the molten soap 377 are cooled using cold air or other cooling means 403. The thus-formed solid tablets 340 are dropped onto conveyor belts 405 and sent to an appropriate packaging operation.

Figure 34:
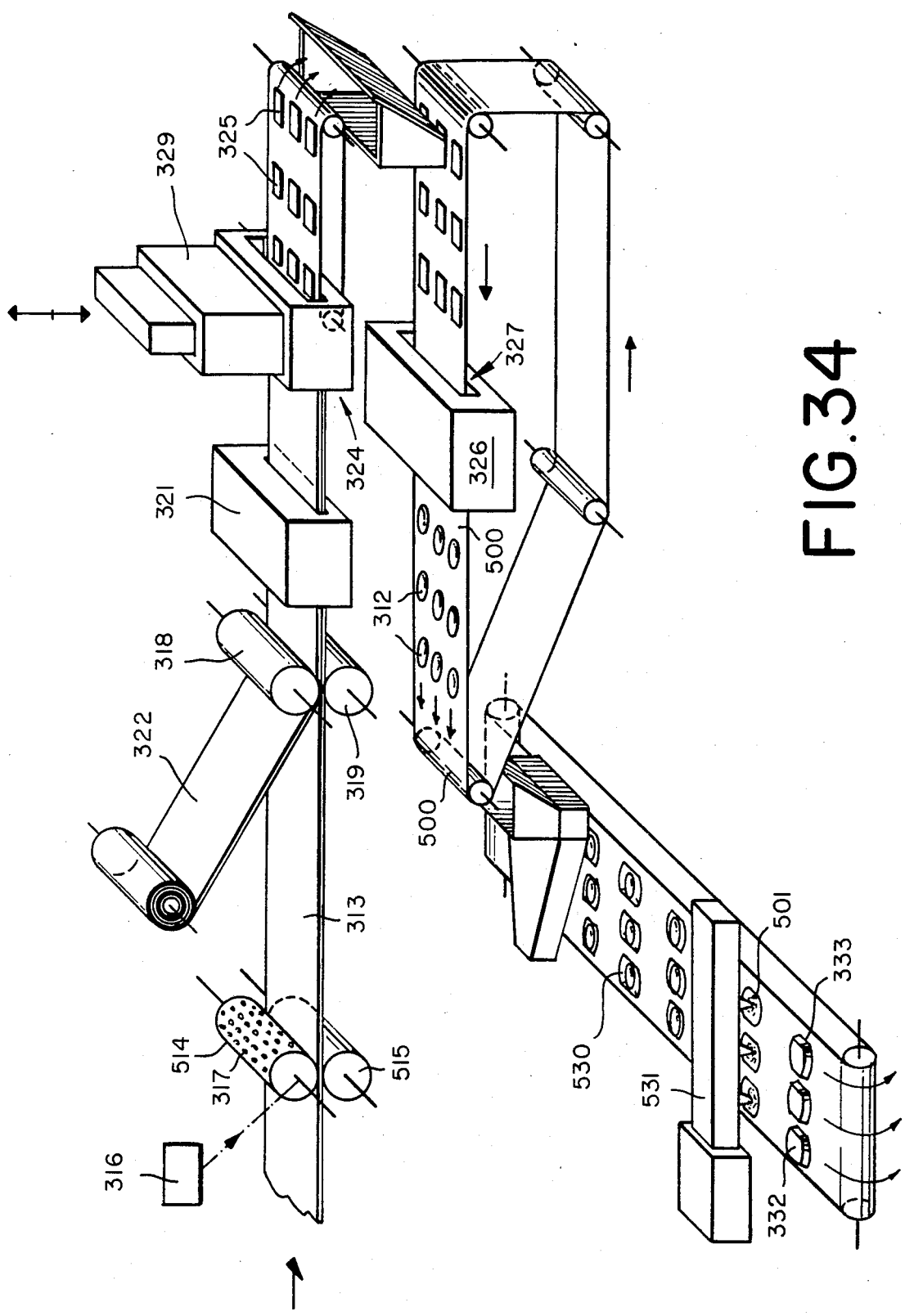
FIG. 34 is a perspective view of another embodiment of apparatus useful in conjunction with our invention showing the formation of the aromatized cores produced from aromatized foamed polymeric pellets produced according to process of our invention, and the formation of molded soap around the cores.
Figure 35:
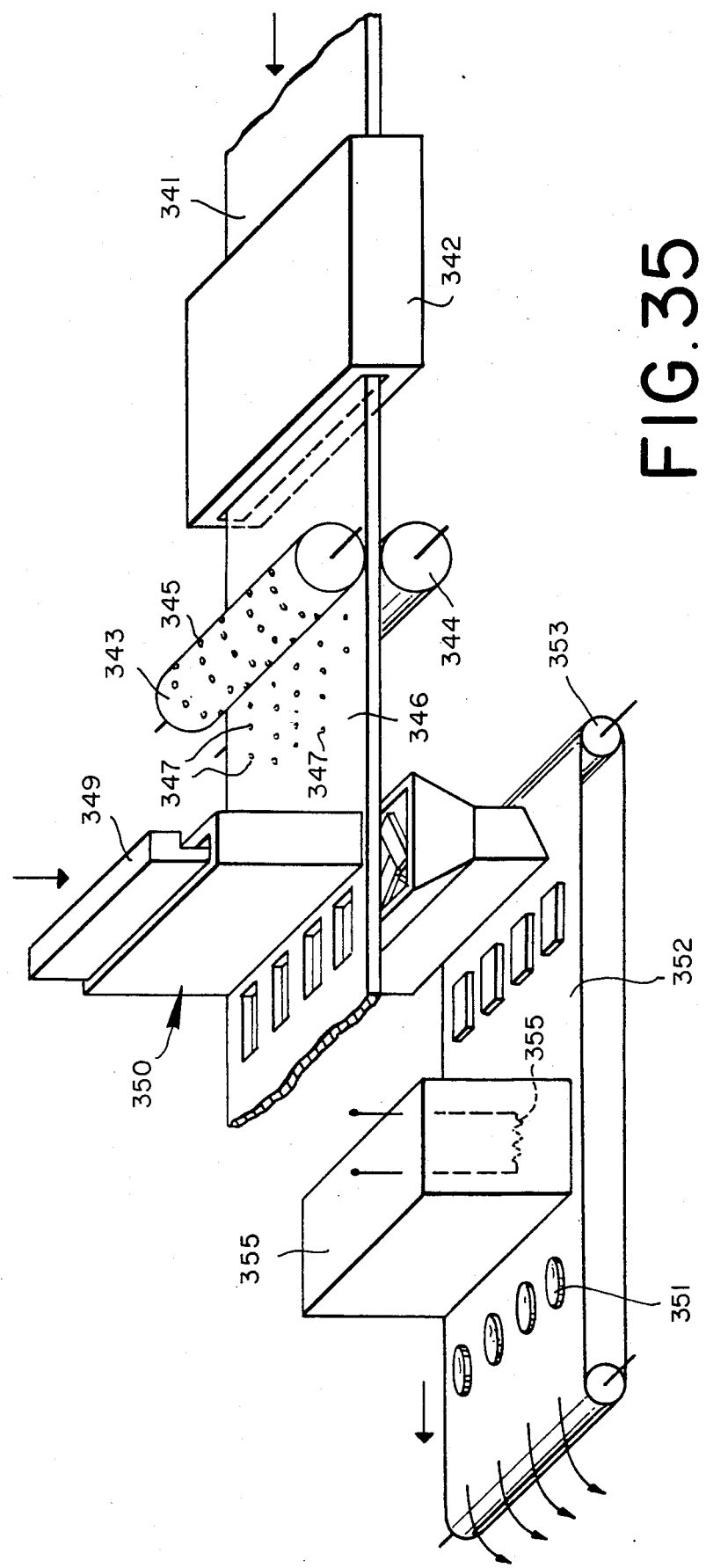
FIG. 35 is a perspective view of another embodiment of the apparatus useful in conjunction with our invention showing the formation of re-aromatized cores on previously-aromatized sheets produced from extruded foamed aroma-containing polymer of our invention.

FIGS. 34 and 35 show in perspective other methods for forming cores 312. Thus, in FIG. 34 two flexible plastic sheets which are foamed produced as a result of extrusion using apparatus of FIG. 2 having thicknesses between 1 cm and 2 cm each and widths of between 3 cm and 50 cm are fed through rollers 318 and 319 after imparting functional fluid (e.g. perfuming) either to one or both sheets using rollers 514 and 515, for example. The functional fluid, e.g. perfume, (in addition to functional fluid previously fed into the extrusion apparatus in FIG. 2) is fed onto the plastic sheets each of which or one of which has interconnected micropores or voids produced using the foaming agent through orifices 317 in the rollers 514 and 515. Thus, solutions at 316 under high pressure are fed through the orifices 317 onto plastic sheets 313 and 322 and into the plastic sheets through the voids therein and micropores therein which are interconnected. The solutions of functional fluid, e.g. perfume, may be solutions in liquid ammonia or more preferably, liquid carbon dioxide at temperatures where the structure of the foamed plastic sheets 313 and 322 will not be physically impaired. The thus-treated sheet (e.g. aromatized sheet) or sheets 313 or 322 are passed through rollers 318 and 319 where they are fused together using heating elements 321. Subsequent to fusing, the thus-formed sheet is cut using cutter 323 at location 324. The cut fused sheets are now in strips 325 which are heated at 327 by heating source 326 in order to eliminate any sharp edges thereby forming cores 312. Cores 312 are then passed onto conveyor belt 500 into cup 330 which is simultaneously filled from filler 331 with molten detergent 501 at such a rate and at such a temperature and having such a viscosity and density that the core 312 is caused to be retained at a location concentrically within the molten soap 332. The thus-formed core-detergent article is cooled so that the detergent surrounding the core solidifies and is in such a state that it is released from the cup 333.

By the same token, a single foamed plastic sheet 341 as is shown in FIG. 35 may be first heated by heating means 342 and then passed through rollers 343 and 344 which are hollow and which have orifices 345 at location 346. Perfuming or aromatizing or other functional fluid material in addition to that added at the time of extrusion, is passed through the orifices 345 under pressure at location 346 into voids or interconnected micropores 347 in the sheet. The sheet is cut at 350 using cutting means 349 and is then passed onto conveyor belt 352 operated by roller 353. The resulting cut plastic containing functional fluid, e.g. perfume 351 is heated to remove any sharp corners at location 354 by heating means 355.

What is claimed is:

1. A process for preparing a perfume-containing foamed polymeric article of manufacture utilizing apparatus comprising a single screw or a twin screw extruder comprising an extruder barrel, said extruder barrel having a multiplicity of barrel segments, located within the extruder barrel, one or two parellel extruder screws, said extruder barrel having a first orifice at the location of a first extruder segment, a second orifice located at a second barrel segment at least one barrel segment downstream from said first barrel segment, and a third orifice located at a third barrel segment at least one barrel segment downstream from said second barrel segment, comprising the steps of:
   (i) extruding a thermoplastic resin with a volatile perfume composition which is compatible with said thermoplastic resin, by adding said thermoplastic resin at said first orifice of said extruder and adding said perfume composition at said second orifice of said extruder, while simultaneously adding downstream from said second orifice, at said third orifice, a gaseous blowing agent selected from the group consisting of nitrogen and carbon dioxide; and
   (ii) then pelletizing the product so extruded
the temperature range in the extruder being from about 160° up to about 240° C.; the feed rate of the resin being from about 80 up to about 300 lbs. per hour into the extruder; the pressure of the gaseous blowing agent at said third orifice being from about 80 up to about 150 psig; the feed rate range of perfume composition at said second orifice being between 1 and 35 percent of the feed rate range of said resin; said thermoplastic resin being compatible with said perfume composition.

2. The process of claim 1 wherein the blowing agent is nitrogen.

3. The process of claim 1 wherein the blowing agent is carbon dioxide.

4. The process of claim 1 wherein the polymer being extruded is low density polyethylene.

5. The process of claim 1 wherein the polymer being extruded is high density polyethylene.

6. The product prepared according to the process of claim 1.

7. Apparatus for the carrying out of a process for preparing a foamed perfume oil containing polymeric article of manufacture comprising an extruder barrel having a multiplicity of barrel segments laterally adjacent one-another and located within the extruder barrel one or two parallel extruder screws, said extruder barrel having three orifices in the wall of the barrel; an upstream orifice located at a first barrel segment, a midstream orifice located at a barrel segment at least one barrel segment downstream from said upstream orifice and a third downstream orifice located at a barrel segment at least one barrel segment downstream from said midstream orifice; connected at the upstream orifice means for adding the thermoplastic polymer into the extruder barrel; connected at the midstream orifice, means for adding liquid perfume composition to the barrel of the extruder; and connected at said third downstream orifice means for adding to the extruder barrel a gaseous blowing agent selected from the group consisting of carbon dioxide and nitrogen under a pressure greater than the pressure within the extruder on operation thereof, said extruder being adapted to operate in a temperature range of from about 150° C. up to about 250° C.; said resin feed means being adapted to feed resin into the barrel of the extruder at a rate of from about 80 up to about 300 lbs. per hour; said blowing agent feed means being adaped to cause the pressure of the blowing agent at said downstream orifice to be from about 80 up to about 150 psig; said liquid perfume composition adding means being adapted to cause the feed rate range of perfume composition at said midstream orifice to be between 1 and 35 percent of the feed rate change of said resin.

8. The apparatus of claim 7 wherein there is contained in the extruder barrel one extruder screw.

9. The apparatus of claim 7 wherein there is contained in the extruder barrel two parallel extruder screws.

* * * * *